United States Patent
Mohapatra et al.

(10) Patent No.: US 9,675,714 B1
(45) Date of Patent: Jun. 13, 2017

(54) GRAPHENE BASED THERANOSTICS FOR TUMOR TARGETED DRUG/GENE DELIVERY AND IMAGING

(71) Applicants: Subhra Mohapatra, Lutz, FL (US); Chunyan Wang, Tampa, FL (US)

(72) Inventors: Subhra Mohapatra, Lutz, FL (US); Chunyan Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 248 days.

(21) Appl. No.: 14/186,845

(22) Filed: Feb. 21, 2014

Related U.S. Application Data

(60) Provisional application No. 61/767,572, filed on Feb. 21, 2013.

(51) Int. Cl.
| | | |
|---|---|---|
| *A61K 51/00* | (2006.01) | |
| *A61M 36/14* | (2006.01) | |
| *A61K 49/18* | (2006.01) | |
| *A61K 31/704* | (2006.01) | |
| *A61K 48/00* | (2006.01) | |
| *A61K 49/00* | (2006.01) | |

(52) U.S. Cl.
CPC ........ *A61K 49/1881* (2013.01); *A61K 31/704* (2013.01); *A61K 48/0041* (2013.01); *A61K 49/005* (2013.01)

(58) Field of Classification Search
CPC ........... B82Y 30/00; B82Y 10/00; B82Y 5/00; C01B 31/0206; C01B 31/0213; C01B 31/0438; C01B 31/043; C01B 31/022; C01B 31/0293; C01B 31/04; C01P 2004/64; Y02E 10/50; A61K 31/704; A61K 48/0041; A61K 49/005; A61K 49/1881
USPC ... 424/1, 1.29, 1.65, 400, 489, 490, 9.1, 9.2, 424/9.3, 9.32, 9.322, 9.323; 428/402, 428/402.2, 402.21, 402.24, 403; 977/773, 977/700, 755, 742, 734, 736, 743, 744, 977/745, 746
See application file for complete search history.

(56) References Cited

PUBLICATIONS

Wang et al, J. Mater. Chem. B. Mater. Biol. Med., Sep. 21, 2013, vol. 1, No. 35, pp. 4396-4405.*
Mendes et al, J. Mater. Chem. B., Oct. 22, 2012, vol. 1, No. 4, pp. 401-428.*
Shen et al, Theranostics, 2012, vol. 2, No. 3, pp. 283-294.*
Bao, et al. "Chitosan-Functionalized Graphene Oxide as a Nanocarrier for Drug and Gene Delivery", Small 7.11 (2011); 1569-578.
Zhang, et al. "Functional Graphaene Oxide as a Nanocarrier for Controlled Loading and Targeted Delivery of Mixed Anticancer Drugs", Small 6.4 (2010); 537-44.
Rana, et al. "Synthesis and Drug-Delivery Behavior of Chitosan-Functionalized Graphene Oxide Hybrid Nanosheets", Macromolecular Materials and Engineering 296.2 (2011); 131-40.
Lee, et al., "Combination Drug Delivery Approaches in Metastatis Breast Cancer", Hindawi Publishing Corporation, Journal of Drug Delivery, vol. 2012, 17 pages.
Sun, et al., "Nano-Graphene Oxide for Cellular Imaging and Drug Delivery", NIP Public Access, National Institute of Health, 2008.
Chen, et al., "Co-Delivery of Doxorubicin and Bcl-2 siRNA by Mesoporous Silica Nanoparticles Enhances the Efficacy of Chemotherapy in Multidrug Resistant Cancer Cells", National Institute of Health, Dec. 2009.
Saad, et al., "Co-Delivery of siRNA and an Anticancer Drug for Treatement of Multidrug-Resistant Cancer", National Institute of Health, Dec. 2008.
Gao, et al., "Nonviral Gene Delivery: What we Know and What is Next", The AAPS Journal 2007; Article 9.
Sun, et al., "Nano-Graphene Oxide for Cellular Imaging and Drug Delivery", NIH Public Access, Mar. 8, 2010.
V. Agrawal, et al., "6-Mercaptopurine and Daunorubicin Double Drug Liposomes—Preparation, Drug-Drug Interaction and Characterization", Liposome Res., 2005, 15, 141-155.
H. Bao, et al., "Chitosan-Functionalized Graphene Oxidemas a Nanocarrier for Drug and Gene Delivery", Small, 2011, 7, 1569-1578.
L. Bacigalupo, et al., "Assessment of liver metastases from colorectal adenocarcinoma following chemotherapy: SPIO-MRI versus FDG-PET/CT" Radiol. Med., 2010, 115, 1087-1100.
C. Wang, et al. "Dual-purpose magnetic micelles for MRI and gene delivery", Journal of Controlled Release, 2012, 163, 82-92.
A. Chen, et al., "Co-delivery of Doxorubicin and Bcl-2 siRNA by Mesoporous Silica Nanoparticles Enhances the Efficacy of Chemotherapy in Multidrug-Resistant Cancer Cells**", Small, 2009, 5, 2673-2677.
B. Chen, et al., "Polyethylenimine-functionalized graphene oxide as an efficient gene delivery vector", Journal of Materials Chemistry, 2011, 21, 7736.
K. Coenegrachts, et al., "Comparison of MRI (including SS SE-EPI and SPIO-enhanced MRI) and FDG-PET/CT for the detection of colorectal liver metastases", European Journal of Radiology, 2009, 19, 370-379.
K. Coenegrachts, et al., "Focal liver lesion detection and characterization: Comparison of non-contrast enhanced and SPIO-enhanced diffusion-weighted single-shot spin echo echo planar and turbo spin echo T2-weighted imaging" European Journal of Radiology, 2009, 72, 432-439.

(Continued)

*Primary Examiner* — D L Jones
(74) *Attorney, Agent, or Firm* — Thomas | Horstemeyer, LLP

(57) ABSTRACT

Disclosed herein are theranostic nanoparticles configured for simultaneous delivery of a diagnostic moiety, drug moiety, and a gene therapy moiety. In one embodiment, the theranostic nanoparticles contain a super paramagnetic iron oxide chemotherapeutic loaded on a chitosan functionalized 2D graphene sheet with a gene therapy moiety attached to the surface of the chitosan functionalized 2D graphene sheet. Also disclosed are methods for making and administering theranositic nanoparticles configured for simultaneous delivery of a diagnostic moiety, drug moiety, and a gene therapy moiety.

8 Claims, 16 Drawing Sheets

(56) References Cited

PUBLICATIONS

H. Cong, et al., "Water-Soluble Magnetic-Functionalized Reduced Graphene Oxide Sheets: In situ Synthesis and Magnetic Resonance Imaging Applications", Small, 2010, 6, 169-173.

L. Feng, et al., "Graphene based gene transfection†", Nanoscale, 2011, 3, 1252-1257.

X. Gao, et al., "Nonviral Gene Delivery: What We Know and What Is Next", AAPS J., 2007, 9, E92-E104.

G. Gollavelli, et al., "Multi-functional graphene as an in vitro and in vivo imaging probe", Biomaterials, 2012, 33, 2532-2545.

B. He, et al., "A Graphene Nanoprobe for Rapid, Sensitive, and Multicolor Fluorescent DNA Analysis" Advanced Functional Materials 2010, 20, 453-459.

H. Hong, et al., "In Vivo Targeting and Imaging of Tumor Vasculature with Radiolabeled, Antibody-Conjugated Nanographene" ACS Nano, 2012, 6, 2361-2370.

S. Hu, et al., "Quantum-Dot-Tagged Reduced Graphene Oxide Nanocomposites for Bright Fluorescence Bioimaging and Photothermal Therapy Monitored In Situ", Advanced Materials, 2012, 24, 1748-1754.

J. Huang, et al., "Mechanism of Cellular Uptake of Graphene Oxide Studied by Surface-Enhanced Raman Spectroscopy", Small 2012, 8, No. 16, 2577-2584.

T. Kaneshiro, et al.,"Targeted intracellular codelivery of chemotherapeutics and nucleic acid with a well-defined dendrimer-based nanoglobular carrier", Biomaterials 30 (2009) 5660-5666.

H. Kim, et al., "Graphene Oxide-Polyethylenimine Nanoconstruct as a Gene Delivery Vector and Bioimaging Tool", Bioconjugate Chem. 2011, 22, 2558-2567.

T. Kuila, et al., "Chemical functionalization of graphene and its applications", Progress in Materials Science 57 (2012) 1061-1105.

O. Mykhaylyk, et al., "Generation of magnetic nonviral gene transfer agents and magnetofection in vitro", Nature Protocols, vol. 2, No. 10, 2007, 2391.

T. Ren, et al., "Engineered polyethylenimine/graphene oxide nanocomposite for nuclear localized gene delivery," Polym. Chem., 2012, 3, 2561.

A.J. Shen, et. al., "Multifunctional nanocomposite based on graphene oxide for in vitro hepatocarcinoma diagnosis and treatment", J. Biomed. Mater. Res., Part A, 2012, 100, 2499-2506.

S. Stankovich, et al., "Graphene-based composite materials", Nature, 2006, 442, 282-286.

L. A. L. Tang, et al., "Graphene-Based SELDI Probe with Ultrahigh Extraction and Sensitivity for DNA Oligomer", J. Am. Chem. Soc., 2010, 132, 10976-10977.

Y. Wang, et al., "Co-delivery of drugs and DNA from cationic core-shell nanoparticles self-assembled from a biodegradable copolymer", Nat. Mater, 2006, 5, 791-796.

W. H. Liu, et. al., "Tumor Necrosis Factor-Related Apoptosis-Inducing Ligand and Chemotherapy Cooperate to Induce Apoptosis in Mesothelioma Cell Lines", Am. J. Respir. Cell Mol. Biol., 2001, 25, 111-118.

K. Wang, et al., "Biocompatibility of Graphene Oxide," Nanoscale Res. Lett., 2011, 6, DOI: 10.1007/s11671-010-9751-6.

Y. Wu, et al., "Carbon Nanotubes Protect DNA Strands during Cellular Delivery", ACSNANO, vol. 2, No. 10, 2023-2028, 2008.

S. Yadav, et al., "Evaluations of combination MDR-1 gene silencing and paclitaxel administration in biodegradable polymeric nanoparticle formulations to overcome multidrug resistance in cancer cells", Cancer Chemother. Pharmacol., 2009, 63, 711-722.

S. Singh, et al., "Amine-Modified Graphene: Thrombo-Protective Safer Alternative to Graphene Oxide for Biomedical Applications", ACS Nano, 2012, 6, 2731-2740.

* cited by examiner

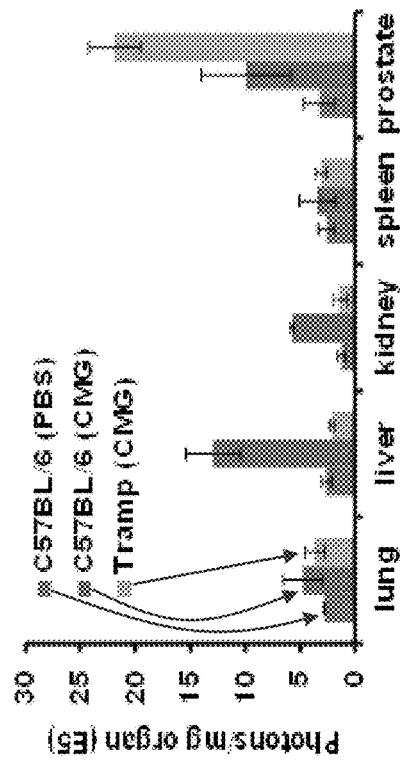
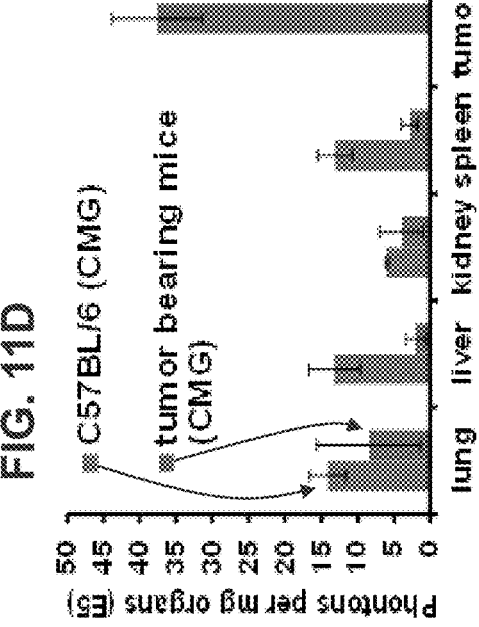
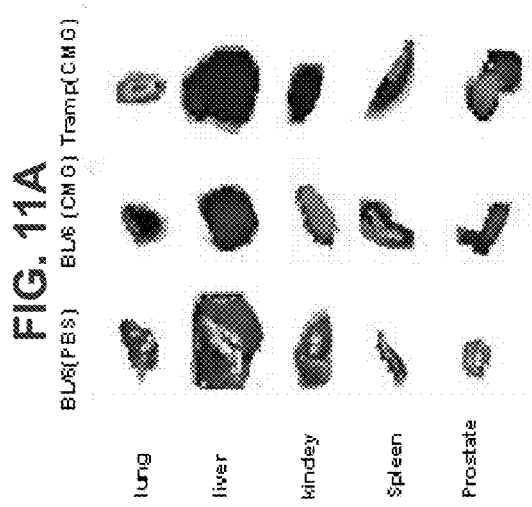
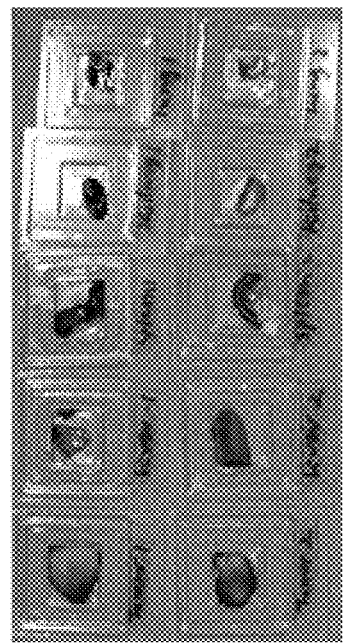

GRAPHENE BASED THERANOSTICS FOR TUMOR TARGETED DRUG/GENE DELIVERY AND IMAGING

CROSS-REFERENCE TO RELATED APPLICATIONS

This application claims the benefit of and priority to U.S. Provisional application Ser. No. 61/767,572, filed on Feb. 21, 2013, having the title "Graphene Based Theranostics for Tumor Targeted Drug/Gene Delivery and Imaging," which is herein incorporated by reference as if expressed in its entirety.

STATEMENT REGARDING FEDERALLY SPONSORED RESEARCH OR DEVELOPMENT

This invention was made with Government support under Contract Nos. RO1CA152005 awarded by the National Institutes of Health. The U.S. Government has certain rights in this invention.

BACKGROUND

Over the past two decades, nanotherapeutics has made a significant impact on the field and success of cancer therapeutics. Despite this, the American Cancer Society estimates that in 2014, there will be an estimated 1.7 million new cancer diagnoses made and an estimated 600,000 deaths attributed to cancer in the United States. Chemotherapy is the most common anticancer treatment, but is frequently discontinued due to toxic side effects or the development of drug resistance. See e.g. Lin et al., Molec. Ther. 2003, 8:441-448.

One strategy to combat drug resistance is to combine at least two chemotherapeutic agents, each having different molecular targets to delay the cancer adaptation process. Another strategy to combat drug resistance is to combine at least two chemotherapeutic agents, each having the same molecular target or otherwise interacting in such a way that the cocktail of chemotherapeutic agents has a greater efficacy and/or target selectivity than any of the individual chemotherapeutics alone. See e.g. Lee and Nan, J. Drug Delivery. 2012. ID 915375. Although in many situations the overall effective dose of each chemotherapeutic is less when administered in a cocktail as compared to administration of each chemotherapeutic individually, discontinuation of combinational therapy due to toxic side effects is still a problem. This is because most combinational therapies are still systemically administered.

Combining traditional drug-based chemotherapy with gene therapy is another promising strategy for the treatment of cancer. See e.g. Lin et al., 2012, Yadav et al., Cancer Chemother. Pharmacol. 2009, 63:711-722, and "Nanomaterials in Drug Delivery, Imaging and Tissue Engineering, ed. Tiwari and Tiwari, Wiley-Scrivener, 2013. Approaches that utilize viral vectors for gene transfer suffer from low transduction efficiencies and their clinical value is diminished as a result of immunogenicity of the vectors, oncogenic risk, and hepatotoxicity. See Gao et al. Aaps J. 2007. 9:E92-E104. Further, these approaches require the gene therapy molecule and the chemotherapeutic molecule to be delivered separately from one another. See e.g. Lin et al., 2012. As such, this approach typically requires increased dosages of both the gene therapy vectors and chemotherapeutic molecule to increase the probability that both molecules end up in the same cells. This results in the potential for increased toxic side effects from the treatment.

MDR-1 targeting small interfering RNA and paclitaxel encapsulated by poly(ethylene oxide)-modified poly(beta-amino ester) or poly(ethylene oxide)-modified (epsilon-caprolactone) nanoparticles, respectively, were shown to increase the cytotoxic activity of paclitaxel in paclitaxel sensitive cancer cells. (Yadav et al., Cancer Chemother. Pharmacol. 2009. 63:711-722). However, this method still does not ensure delivery to the same cell as the gene therapy molecule and the chemotherapeutic drug are still delivered on separate platforms.

A few preliminary in vitro research efforts have focused on simple non-viral vectors for simultaneous drug and gene therapy, such as cationic liposomes (e.g. Saad et al., Nanomed. 2008. 3:761-776), cationic core-shell nanoparticles (e.g. Wang et al., Nat. Mater. 2006. 5:791-796), cationinc micells (e.g., Zhu et al., Biomaterial. 2010.31:2408-2416), dendrimers (e.g. Kaneshio and Lu. Biomaterial. 2009. 30:5660-5666), and mesoporous silica nanoparticles (e.g. Chen et al. Small. 2009. 5:2673-2677. Although these combination therapies are more effective at killing cancer cells than the chemotherapeutic drugs alone, they are also more likely to damage healthy tissue when delivered systemically. Therefore, there exists a need for targeted delivery of therapeutic agents, including combination therapies, to improve therapeutic efficacy while reducing toxic side effects.

Additionally, heterogeneity of cancers makes it difficult to predict which therapy or combination of therapies will be efficacious for a particular cancer in an individual. Therefore, it is common that a patient may have to try several treatment regimens before one (if any) are found to be effective. This often leads to noncompliance with therapy and poor success rates. In some instances, the tumors are biopsied and tested for drug resistance and sensitivities in vitro. However, results from in vitro drug efficacy studies, even on biopsied tumors, are of limited value because they do not effectively mimic the in vivo tumor environment. Further, biopsy assays do not permit for non-invasive monitoring of the effectiveness of a treatment regimen.

As such there is an urgent need to develop a single platform that can efficiently deliver therapeutic drugs and gene therapy molecules that allow for non-invasive treatment monitoring.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 11A-11D show the biodistribution analysis of Cy5.5-CMG nanoparticles in tissues after administration to mice. Mice (n=2 per group) were injected with Cy5.5-CMG nanoparticles (about 500 µL sample with 500 µg CMG and 6.25 µg Cy5.5) nanoparticles or PBS (control) via I.P. injection. 4 h post injection, mice were sacrificed and organs were collected and imaged via Xenogen IVIS® imager to measure fluorescence. Average fluorescence intensity of each organ was normalized to the weight of each organ. FIG. 11A shows the representative fluorescence images from injected C57BL/6 and TRAMP mice. FIG. 11B shows average fluorescence intensity of each organ from injected C57BL/6 and TRAMP mice. FIG. 11C shows the representative fluorescence images from injected C57BL/6 and Lewis lung carcinoma 1 (LLC1) Tumor bearing mice. FIG. 11D shows average fluorescence intensity of each organ from injected C57BL/6 and LLC1 Tumor bearing mice.

DETAILED DESCRIPTION

Figure 1:
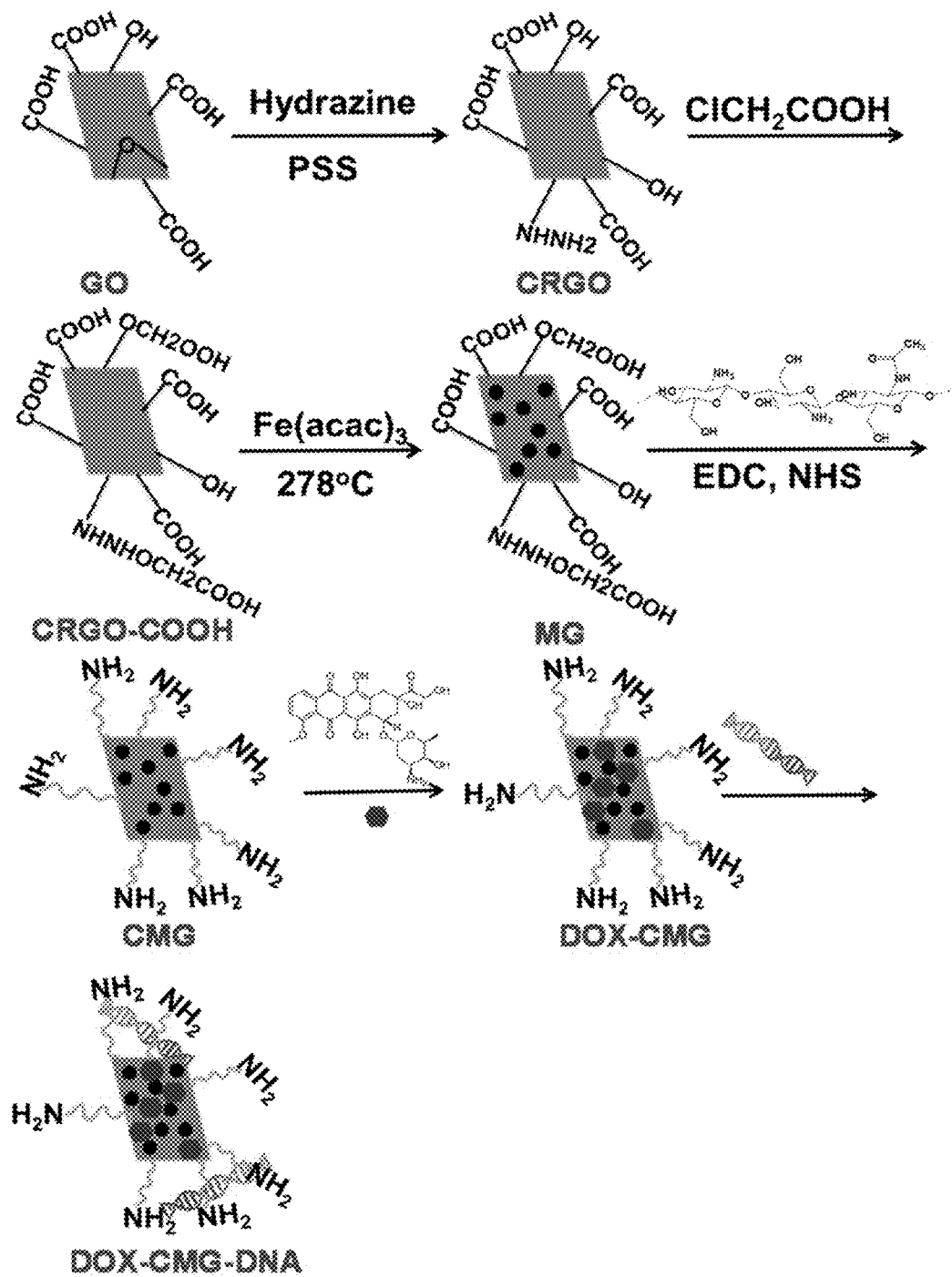
FIG. 1 shows one embodiment of synthesis of a doxorubicin-Chitosan functionalized magnetic graphene (CMG)-DNA nanoparticle.

Delivering multiple drugs or therapies with a single nanoplatform is promising, yet remains to be fully realized. One reason that single nanoplatforms have not been effective is that entrapment efficiency of the drug compound by nanoparticles is typically low. Further, dissimilar pharmacokinetics of different drug molecules make it difficult to create effective combinations. Disclosed herein are embodiments encompassing a single theranostic nanoparticle platform that delivers a drug molecule and a gene therapy molecule, wherein the nanoparticle also allows for non-invasive determination of treatment efficacy. Also disclosed herein are methods of generating the nanoparticles and methods of treating a subject in need thereof. Term definitions used in the specification and claims to described the claimed invention are as follows.

Definitions

As used herein, "theranostic" refers to the ability of a compound, molecule, or formulation to act simultaneously as a therapeutic agent and as a diagnostic agent. As such, a "theranostic agent" is an agent that functions as a therapeutic agent and as a diagnostic agent.

As used herein, "graphene" refers to a two-dimensional (2D), crystalline allotrope of carbon, which contains densely packed carbon atoms in a regular $sp^2$-bonded atomic scale hexagonal pattern.

As used herein, "effective dose" or "effective amount" refer to an amount sufficient to effect beneficial or desired results. An effective dosage or amount can be administered in one or more administrations, applications, or dosages.

As used herein, "chemotherapeutic agent" or "chemotherapeutic" refer to a therapeutic agent utilized to prevent or treat cancer.

As used herein, "gene therapy moiety" refers to a molecule capable of modifiying, either directly or indirectly, the transcription or translation of an RNA transcript and/or function or activity of a specific protein.

As used herein, "drug moiety" refers to a therapeutic molecule that is attached as a functional group to another compound, such as the nanoparticles described herein.

As used herein, "control" is an alternative subject or sample used in an experiment for comparison purposes and included to minimize or distinguish the effect of variables other than an independent variable.

As used herein, "nanoparticle" refers to any entity having a greatest dimension (diameter or length, width or height) of less than 100 microns (µm). Nanoparticles having a spherical shape are generally referred to as "nanospheres."

As used herein, "functionalization moiety" refers to a compound or molecule that is capable of improving or otherwise modifying the solubility of the nanoparticle disclosed herein, modifying the biocompatibility of the nanoparticle, increasing or otherwise modifying the loading and/or attachment capacity of the nanoparticle, and/or controlling the release of or otherwise activating the drug moiety, gene therapy moiety, and/or diagnostic moiety.

As used herein, "subject" or "patient" refers to any organism to which the nanoparticles described herein may be administered, e.g., for experimental, theranositic, therapeutic, diagnostic, and/or prophylactic purposes. "Subjects" include animals, including mammals such as mice, rats, rabbits, non-human primates, and humans, as well as plants.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "plasmid" as used herein refers to a non-chromosomal double-stranded DNA sequence including an intact "replicon" such that the plasmid is replicated in a host cell.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA or viral DNA, or may contain elements of both.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "specific binding partner" is a compound or molecule to which a second compound or molecule binds with a higher affinity than all other molecules or compounds.

As used herein, "protein substrate" or "enzyme substrate" refers to a molecule upon which a protein acts.

As used herein, "ligand" refers to a compound or molecule that binds specifically and reversibly to another chemical or biologic entity to form a larger complex.

As used herein, "pharmaceutically acceptable carrier" refers to diluent, adjuvant, excipient, or vehicle with which an active agent, chondrocytes of the present disclosure, or composition containing chondrocytes of the present disclosure is administered in conjunction with and which is approved by a regulatory agency of the Federal or a state government or listed in the U.S. Pharmacopeia or other generally recognized pharmacopeia for use in animals and/or humans.

As used herein "immunomodulator," refers to an agent, such as a therapeutic agent, which is capable of modulating or regulating one or more immune function or response.

As used herein, "targeting moiety" refers refers to a moiety that localizes to or away from a specific local.

As used herein, "therapeutic agent" refers to an agent that can be administered to prevent or treat a disease or disorder.

As used herein, "therapeutically effective amount" is synonymous with "therapeutic efficacy" and refers to an amount of a therapeutic agent that, when incorporated into and/or onto nanoparticles described herein, produces some desired effect at a reasonable benefit/risk ratio applicable to any medical treatment. The effective amount may vary depending on such factors as the disease or condition being treated, the particular targeted constructs being administered, the size of the subject, or severity of the disease or condition.

As used herein, "incorporated with" or "loaded onto," as used in connection with NGS, refers to the interaction between a moiety and the NGS.

Unless otherwise defined herein, all technical and scientific terms used herein have the same meaning as commonly understood by one of ordinary skill in the art.

Discussion

Nanoparticles according to the embodiments contain at least one (2D) nanographene sheet (NGS) with one or more functionalization moiety, drug moiety, gene therapy moiety, and/or diagnostic moiety attached to a surface of the NGS. In one aspect, the nanoparticles described herein contain a drug moiety, a gene therapy moiety, and a diagnostic moiety. As such, the disclosed nanoparticles can act as theranostic agents and therefore, facilitate simultaneous treatment and diagnostic monitoring of treatment efficacy.

Theranostic Nanoparticles and Theranostic Nanoparticle Formulations

In one embodiment, the NGS is a chemically reduced graphene oxide (CRGO) sheet. CRGO sheets have the advantage over graphene oxide (GO) sheets in that CRGO sheets are less toxic than GO sheets. Indeed, GO is not readily cleared by the kidneys and exhibits dose-dependent toxicity to cells in vitro and in animals. See e.g. Wang et al., Nanoscale Research Letters. 2011:6:8. In some embodiments, the nanoparticles have a greatest dimension of about 1000 nm or less. In other embodiments, the nanoparticles have a greatest dimension of about 500 nm or less. In further embodiments, the nanoparticles have a greatest dimension of about 100 nm or less. In some embodiments, a population of nanoparticles are substantially uniform in terms of size, shape, charge, and/or composition. In other embodiments, a population of nanoparticles are not substantially uniform in terms of size shape, charge, and/or composition.

The nanoparticles described herein can also contain at least one functionalization moiety attached to a surface of the CRGO sheet. In some embodiments, the functionalization moiety operates to, inter alia, improve or otherwise modify the solubility of the nanoparticle, modify the biocompatibility of the nanoparticle, increase or otherwise modify the loading capacity of the nanoparticle, and control the release of or otherwise activate the drug moiety, gene therapy moiety, and/or diagnostic moiety. Examples of such functionalization moieties include, but are not limited to, chitosan (or chitin) chondroitin sulfate, dextran sulfate, carboxymethyl dextran, alginic acid, pectin, carragheenan, fucoidan, agaropectin, porphyran, karaya gum, gellan gum, xanthan gum, hyluronic acids, glucosamine, galactosamine polyglutamic acid, polyaspartic acid, poly lactic acid, lysozyme, cytochrome C ribonuclease, trypsinogen, chymotrypsinogen, α-chymotrypsin, polylysine, polyarginine, histone, protamine, ovalbumin, dextrin, cyclodextrin, polyethylene glycol, polyethlyleneimine, and poly(sodium-4-styrenesulfonate). In some embodiments, chitosan is used to functionalize the CRGO sheet. In other embodiments, chitosan and a functionalization moiety selected from polyglutamic acid, polylactic acid, polyaspartic acid, polyethylene glycol, poly(sodium-4-styrenesulfonate), and/or polyethyleneimine.

The nanoparticles described herein can also contain at least one drug moiety attached to a surface of the CRGO sheet. Examples of drug moiety include, but are not limited to chemotherapeutic agents, analgesics, anesthetics, anti-inflammatory agents, including steroids and non-steroidal anti-inflammatory agents, antihistamines, anti-infective agents, antineoplastic agents, blood derivatives, blood formation agents, coagulation agents, thrombosis agents, immunomodulators, antibodies, aptamers, and/or antipyretics.

In a one embodiment, the nanoparticles contain at least one chemotherapeutic attached to a surface of the CRGO. Examples of chemotherapeutic agents include, but are not limited to, alkylating agents such alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1 065 (including its adozelesin, carzelesin and bizelesin synthetic analogues); cryptophycins (particularly cryptophycin 1 and cryptophycin 8); dolastatin; duocarmycin (including the synthetic analogues, KW –2189 and CB 1-TM 1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; Spiro germanium; tenuazonic acid; triaziquone; 2,2',2"-trichlorotriethylamine; trichothecenes (especially T-2 toxin, verracurin A, roridin A, and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

In some embodiments, the drug moiety is attached to a surface of the NGS via covalent bonds. In other embodiments, the drug moiety is releasably attached to the surface of the NGS. In some embodiments, the drug moiety is releasably attached to the surface of the NGS through a cleavable linker molecule. In other embodiments, the drug moiety is attached through non-covalent interactions, such as hydrogen boding, electrostatic, Tr-effects, van der Waals forces, and hydrophobic effects. In some embodiments, the attachment of the drug moiety to a surface of the NGS is configured so as to allow for controlled or delayed release of the drug moiety from the NGS. In other embodiments, the attachment of the drug moiety to a surface of the NGS is configured so as to allow for a bolus release of the drug moiety from the NGS. In further embodiments, the drug moiety is incorporated within or loaded onto the 2D graphene sheet.

The nanoparticles described herein can also contain at least one gene therapy moiety attached to a surface of the NGS. In one embodiment, the gene therapy moiety sensitizes a cell such that a drug moiety has increased efficacy, as compared to the drug moiety alone. In some embodiments, the gene therapy moiety controls the expression of a region of genomic DNA through direct modulation of the transcription of genomic DNA, the translation of an RNA transcript, or otherwise modifies the function or activity of a specific protein of interest. For example, the gene therapy moiety can be a small interfering RNA molecule that modulates the transcription and/or translation of a particular DNA segment or RNA transcript. In other embodiments, the gene therapy moiety acts indirectly to modulate the transcription of genomic DNA, translation of an RNA transcript, or modify the function or activity of a specific protein of interest. For example, the gene therapy moiety can be configured to suppress a co-factor of the protein of interest, without which the protein of interest has reduced activity.

Examples of a gene therapy moiety include, but are not limited to, naked DNA, DNA plasmids, DNA vectors, viral DNA vectors, non-viral DNA vectors, RNA including but not limited to, tRNA, mRNA, miRNA, siRNA, piRNA, and shRNA, peptides, polypeptides, proteins, fragments thereof, and combinations thereof.

In some embodiments, the gene therapy moiety is attached to a surface of the NGS via covalent bonds. In other embodiments, the gene therapy moiety is releasably attached to the surface of the NGS. In some embodiments, the gene therapy moiety is releasably attached to the surface of the NGS through a cleavable linker molecule. In other embodiments, the gene therapy moiety is attached through non-covalent interactions, such as hydrogen boding, electrostatic, Tr-effects, van der Waals forces, and hydrophobic effects. In some embodiments, the attachment of the gene therapy moiety to a surface of the NGS is configured so as to allow for controlled or delayed release of the gene therapy moiety from the NGS. In other embodiments, the attachment of the gene therapy moiety to a surface of the NGS is configured so as to allow for a bolus release of the gene therapy moiety from the NGS. In further embodiments, the gene therapy moiety is incorporated within or loaded onto the 2D graphene sheet.

The nanoparticles described herein can also contain at least one diagnostic moiety attached to a surface of the NGS. The diagnostic moiety can be any suitable compound or molecule that allows for non-invasive determination of treatment efficacy. In some embodiments, the diagnostic moiety is a magnetic resonance imaging (MRI) contrast agent. The contrast agent can be a T1 or a T2 contrast agent. It is preferable that the contrast agent be sensitive enough to allow for determination of treatment efficacy. Examples of suitable MRI contrast agents include, but are not limited to, gadolinium or a gadolinium-containing agent, a superparamagnetic iron oxide (SPIO), supreparamagnetic iron platinum (SIPP), and/or paramagnetic manganese. In other embodiments, the diagnostic moiety is a radio contrast agent suitable for use in X-ray imaging techniques such as radiography or computed tomography (CT). Suitable radio contrast agents include, but are not limited to, radioactive isotopes of sodium, phosphorus, iodine, gold, iron, copper, potassium, and arsenic, as well as dyes, including but not limited to indigocarmine and fluorescein. In one embodiment, the diagnostic moiety is SPIO. In further embodiments, the gene therapy moiety is incorporated within or loaded onto the 2D graphene sheet.

In some embodiments, the diagnostic moiety is attached to a surface of the NGS via covalent bonds. In other embodiments, the diagnostic moiety is releasably attached to the surface of the NGS. In some embodiments, the diagnostic moiety is releasably attached to the surface of the NGS through a cleavable linker molecule. In other embodiments, the diagnostic moiety is attached through non-covalent interactions, such as hydrogen boding, electrostatic, 1T-effects, van der Waals forces, and hydrophobic effects. In some embodiments, the attachment of the diagnostic moiety to a surface of the NGS is configured so as to allow for controlled or delayed release of the diagnostic from the NGS. In other embodiments, the attachment of the diagnostic moiety to a surface of the NGS is configured so as to allow for a bolus release of the diagnostic moiety from the NGS.

Targeted delivery can be achieved by the addition of ligands or other targeting moieties to the nanoparticle. It is contemplated that this may enable delivery to specific cells, tissues, organs or foreign organisms. In some embodiments, the nanoparticles also include a targeting moiety attached to a surface of the NGS. Examples of a targeting moiety include, but are not limited to, antibodies, antibody fragments such as antigen-binding fragments, as well as full-length monomeric, dimeric or trimetric polypeptides derived from antibodies, aptamers, and protein substrates, ligands, or specific binding partners. In some embodiments, the targeting moiety is an antibody specific for a cancer antigen. Example cancer antigens include, but are not limited to Melan-A/MART-1, dipeptidyl peptidase IV, adenosine deaminase-binding protein, cyclophilin b, colorectal associated antigen-C017-1A/GA733, carcinoembryonic antigen and its immunogenic epitopes CAP-1 and CAP-2, etv6, am11, prostate specific antigen and its immunogenic epitopes, PSA-1, PSA-2, and PSA-3, prostate-specific membrane antigen. T-cell receptor/CD3-zeta chain, MAGE-family of tumor antigens, GAGE-family of tumor antigens, BAGE, RAGE, LAGE-1, NAG, Gn-T, MUM-1, CDK4, tyrosinase, p53, MUC family, HER2/neu, p21 ras, RCAS1, α-fetoprotein, E-cadherin, α-catenin, β-catenin, γ-catenin, p120ctn, gp100$^{pmel117}$, PRAME. NY-ESO-1, brain glycogen phosphorylase, SSX-1, SSX-2, (HOM-MEL-40), SSX4, SSX-5, SCP-1, CT-7, cdc27, adenomatousm, polyposis coli protein, fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen-1, and/or c-erb B-2.

In some embodiments, the targeting moiety is attached to a surface of the NGS via covalent bonds. In other embodiments, the targeting moiety is releasably attached to the surface of the NGS. In some embodiments, the targeting moiety is releasably attached to the surface of the NGS through a cleavable linker molecule. In other embodiments, the targeting moiety is attached through non-covalent interactions, such as hydrogen boding, electrostatic, π-effects, van der Waals forces, and hydrophobic effects. In some embodiments, the attachment of the targeting moiety to a surface of the NGS is configured so as to allow for controlled or delayed release of the diagnostic from the NGS. In other embodiments, the attachment of the targeting moiety to a surface of the NGS is configured so as to allow for a bolus release of the targeting moiety from the NGS.

Where clinical application of the disclosed nanoparticles is undertaken, it will generally be beneficial to prepare the nanoparticles as a pharmaceutical formulation appropriate for the intended application. As such, in some embodiments, the pharmaceutical formulation containing theranostic nanoparticles is essentially free of pyrogens, as well as any other impurities that could be harmful to humans or animals. In some embodiments where the nanoparticles are contained in a pharmaceutical formulation, the formulation includes a pharmaceutically acceptable carrier. In some embodiments the pharmaceutical carriers are liquids, such as water or and oils, including those of petroleum, animal, vegetable, or synthetic origin, such as peanut oil, soybean oil, mineral oil, sesame oil, and the like. In other embodiments, the pharmaceutically acceptable carrier is gum acacia, gelatin, starch paste, talc, keratin, colloidal silica, urea, and the like.

In other embodiments, the pharmaceutically acceptable carrier is saline solution, aqueous dextrose solution, or glycerol solutions. These embodiments are particularly useful for injectable compositions. In further embodiments, the pharmaceutically acceptable carrier includes an excipient, such as glucose, lactose, sucrose, glycerol monostearate, sodium chloride, glycerol, propylene, glycol, water, ethanol and combinations thereof. In some embodiments, the compositions can contain an amount of wetting or emulsifying agents, or pH buffering agents. The present compositions my take the form of solutions, emulsions, sustained-release formulations, or any other form suitable for use.

In certain embodiments, the pharmaceutical composition contains, for example, at least about 0.1% of the nanoparticles described herein. In other embodiments, the nanoparticle may be between about 1% to about 75% of the weight of the composition, or between about 5% to about 50%, and any range derivable therein. In further embodiments, a dose of the pharmaceutical composition containing nanoparticles described herein, is about 1 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 50 milligram/kg/body weight, about 100 milligram/kg/body weight, or more per administration, and any range derivable therein.

A nanoparticle, as disclosed herein, may be administered in a dose of about 0.001 to about 100 or more mg of nanoparticle per dose. Each dose may be in a volume of about 1 to about 10 µl, about 10 µL to about 100 µL, about 100 µL to about 500 µL, about 500 µL to about 1000 µL, about 1 mL to about 5 mL, 5 mL to about 10 mL, 10 mL to about 100 mL, 100 mL to about 1 L or more.

The quantity of the theranostic nanoparticle or nanoparticle formulation to be administered, both according to number of treatments and dosage, depends on the protection or effect desired. Precise amounts of the theranostic nanoparticle or nanoparticle formulations also depend on the judgment of the practitioner and are peculiar to each individual. Further, the precise amounts of the thearnositc nanoparticle, in both treatment regimen and dosage, may change over the course of treatment as discussed below. Factors affecting the dose include, but are not limited to, the physical and clinical state of the patient, the administration route, intended goal of treatment (e.g., alleviation of symptoms versus cure) and the potency, stability, and toxicity of the particular compound or compounds associated with or attached to a surface of the NGS.

Generation of Theranostic Nanoparticles

Methods for producing theranostic nanoparticles are described herein. In some embodiments, the method involves creating 2D graphene sheets having at least a diagnostic moiety, a drug moiety, and a gene therapy moiety attached or otherwise loaded onto the 2D graphene sheet(s). In further embodiments, the 2D graphene sheet includes a functionalization moiety, which functionalizes the 2D graphene sheet. One of ordinary skill will appreciate that the exact process by which the nanoparticles are generated will depend on, inter alia, the exact moieties being attached or incorporated with the 2D graphene sheet as this will dictate the chemical processes used and the order in which they are performed. These processes are within the scope of and spirit of this disclosure as they can be applied to molecules disclosed herein.

In one embodiment, where theranostic nanoparticles contain a SPIO diagnostic moiety, a chemotherapeutic drug moiety, a DNA gene therapy moiety, and a chiotsan functionalizing moiety, the method of generating the nanoparticle begins by reducing GO sheets in the presence of poly(sodium-4-styrenesulfonate) (PSS) to form PSS-coated CRGO sheets. More specifically, GO was reduced in the presence of PSS and hydrazine under reflux at a temperature of about 100° C. to form PSS coated CRGO-OH sheets.

After cooling to room temperature, the CRGO-OH sheets are converted to CRGO-COOH sheets using a procedure modified from that disclosed in Sun et al., Nano. Res. 2008. 1:203-212. Briefly, CRGO-COOH is centrifuged for about 30 min and the freeze dried. The freeze dried CRGO-COOH is then dispersed in triethylene glycol by ultra-sonication for about 30 min at room temperature. After ultra-sonication, $Fe(acac)_3$ is then added to the suspension and the suspension is refluxed at about 278° C. for about 1 h with stirring under argon gas to load the diagnostic moiety onto the graphene sheet. This produces magnetic graphene (MG).

After cooling to room temperature, the MG is precipitated, washed in ethanol, and dispersed in water at room temperature. To attach the chitosan to the MG and functionalize the MG, MG is activated by incubating the MG with 1-Ethyl-3-(3-dimethylaminopropyl)carbodiimide (EDC) and N-Hydroxysuccimide (NHS) in water for about 30 minutes. Next, chitosan is added to the activated MG. The chitosan was kept in reaction with the MG for about 3 h and follow by dialyzation against deionized water for about 2 days. This forms a chitosan functionalized MG sheet (CMG sheet).

In some embodiments, a drug moiety is then loaded onto the CMG sheet by incubating the functionalized MG sheet in an excess of the drug moiety, such as doxorubicin. In one embodiment, the reaction between the CMG sheet and the drug moiety proceeds overnight with shaking at about 4° C. Unbound drug moiety is removed by dialysis against deionized water for about 24 h. As discussed previously, the exact mechanism of attachment or loading of the drug moiety will depend mainly on the exact drug moiety being incorporated or attached to the CMG sheet.

In some embodiments, a gene therapy moiety is added to the drug-loaded CMG sheet. For some embodiments, DNA, particularly plasmid DNA, is attached to the drug-loaded CMG sheet by adding the DNA dropwise to a CMG solution and vortexed for about 20 minutes. The weight ratio of the CMG to DNA can range from about 1:1 to about 10:1. In some embodiments, the weight ratio of the CMG to DNA is about 5:1.

In some embodiments, a targeting moiety is used to increase specificity of the theranostic and to reduce systemic side effects. The targeting moiety can be attached or loaded onto the CMG using methods known in the art. For example, antibodies and other proteins, such as ligands or substrates, can be attached using crosslinking or disulfide linking groups. More details of the methods for generating theranostic nanoparticles are discussed in connection with the Examples below.

Administration and Use of Theranostic Nanoparticles

The nanoparticles and nanoparticle formulations are administered in an amount effective to provide the desired level of biological, physiological, pharmacological, preventative, and/or therapeutic effect, while also permitting diagnostic determination of treatment efficacy. Preferably, the diagnostic determination is completed using non-invasive methods, such as MRI or CT. Nanoparticles and nanoparticle formulations of the disclosed embodiments are ideal for a number of theranostic applications including as anittumor, antibacterial, and antiviral theranostic agents. A key advantage of the disclosed theranostic nanoparticles is that they permit evaluation of therapy efficacy non-invasively and under in vivo conditions.

In some embodiments, the nanoparticle may stimulate or inhibit a biological or physiological activity (e.g. tumor development). The amount of the nanoparticle administered should not be so great that the composition has a consistency that inhibits delivery to the administration site by the desired method i.e. I.V. or I.P. The lower limit of the amount of the nanoparticle depends on, inter alia, its activity and the period of time desired for treatment.

A nanoparticle or nanoparticle formulation according to the embodiments may be administered, for example, I.V., intradermally, intraarterially, intraperitoneally (I.P.), intralesionally, intracranially, intraarticularly, intraprostaticaly, intrapleurally, intratracheally, intravitreally, intravaginally, intrarectally, intratumorally, intramuscularly, subcutaneously, subconjunctival, intravesicularly, mucosally, intrapericardially, intraumbilically, intraocularally, orally, locally, by injection, by infusion, by continuous infusion, by localized perfusion bathing target cells directly, via catheter, or lavage. In one embodiment, the nanoparticle or nanoparticle formulation is administered by I.V. injection. In other embodiments, the nanoparticle or nanoparticle formulation is administered by I.P. injection.

In one embodiment, nanoparticles having a functionalization moiety, a drug moiety, and a gene therapy moiety attached to a surface are administered to a subject followed by applying a magnetic field (e.g. a static magnetic field) to the subject, wherein the field applied to the subject is effective to image cells treated with the nanoparticles. In some embodiments, the effectiveness of the nanoparticle treatment can be determined. The medical practitioner can then adjust treatment regimen accordingly, based on the diagnostic results obtained. In other embodiments, after administration of the nanoparticles having a functionalization moiety, a drug moiety, and a gene therapy moiety attached to a surface, the patient undergoes a radiograph or CT-scan. Like before, the medical practitioner can then adjust the treatment regimen accordingly, based on the diagnostic results.

EXAMPLES

Example 1: Preparation and Characterization of CMG Nanoparticles

Materials and Methods

Water-soluble chitosan (10 KDa, about 50 nm) was a gift from Transgenex Nanobiotech Inc. Tampa, Fla. Hydrazine, 1-ethyl-3-(3-dimethylaminopropyl) carbodiimide (EDC), N-hydroxysuccinimide (NHS) and poly(sodium-4-styrene-sulfonate) (PSS, Mw70,000) were purchased from Sigma-Aldrich. Graphite oxide (GO) was bought from Angstron Materials. Doxorubicin hydrochloride was obtained from LC Laboratories. Iron (III) acetylacetonate ($Fe(AcAc)_3$), oleic acid, and triethylene glycol were purchased from Acros Organics. Cy5.5-NHS was bought from Lumiprobe Corporation.

Preparation of CMG-Nanoparticles

PSS-coated CRGO sheets were prepared by reduction of GO (1 mg mL$^{-1}$) in the presence of PSS (15 mg mL$^{-1}$) and 1.5 ml hydrazine under refluxing at 100° C. See Chen et al., J. Mater. Chem. 2011.21:7736-7741. After cooling to room temperature, about 1.2 g of NaOH and about 1.0 g of chloroacetic acid were added to the above solution and bath-sonicated for about 3 h (See e.g., He et al., Adv. Funct. Mater. 2010. 20:453-459) to convert CRGO-OH to CRGO-COOH using protocol as described with some modifications. The CRGO-COOH suspension was centrifuged at about 4996 g force for about 30 min at room temperature and the sample was freeze-dried. CRGO-COOH (about 10 mg) was dispersed in about 10 ml triethylene glycol by ultra-sonication for about 30 min at room temperature and about 20 mg of Fe(acac)$_3$ was then added to the suspension. The mixture was refluxed at about 278° C. for about 1 h with stirring under argon gas. After cooling to room temperature, the CRGO decorated with iron nanoparticles (magnetic-graphene, MG) was precipitated, washed with ethanol, and dispersed in water at room temperature. To covalently bond chitosan to MG, a suspension of about 3 mg MG was activated with EDC (about 53.7 mg) and NHS (about 55.3 mg) in about 1 ml water for about 30 min and added to about 10 ml of an aqueous solution of about 150 mg of water-soluble chitosan. The reaction was kept at room temperature for about 3 h and then dialyzed for two days using a dialysis membrane (SpectraPor Biotech, cellulose ester, 1000 Dalton MWCO) against about 5 L deionized water. To determine the structure of the synthesized nanoparticles, FTIR spectra were obtained using a NEXUS spectrometer.

Measurement of Particle Size and Distribution

The hydrodynamic particle sizes and distribution of various graphene-based nanoparticles in water were measured at about 25° C. using a DynaPro DLS plate reader (Wyatt Technology, Germany).

MRI Phantom Imaging

Various dilutions of CMG nanoparticles were made with about 100 μl of about 0.5% agarose gel and placed in a 96-well plate. The concentration of iron in the CMG nanoparticles was determined according to the method of Mykhaylyk (Mykhaylyk et al., Nature Protocols. 2007.

2:2391-2411). MR images were obtained using an Agilent ASR310 7-Tesla, high-field MRI scanner. Multi-echo transverse relaxation experiments (MEMS) were performed in imaging mode to determine $T_2$ values. Nonlinear least-square fitting was performed with MATLAB (Mathworks, Inc.) on a pixel-by-pixel basis. A region of interest (ROI) was drawn for each well, where the mean value was used to determine the transverse molar relaxivity $r_2$. The image was recorded with Vnmrj 3.0.

Statistical Analysis

Statistical analysis of the data was carried out using Student's t-test. Data are expressed as means plus or minus standard deviation. Difference was considered statistically significant when the $p<0.05$.

Results

Figure 2:
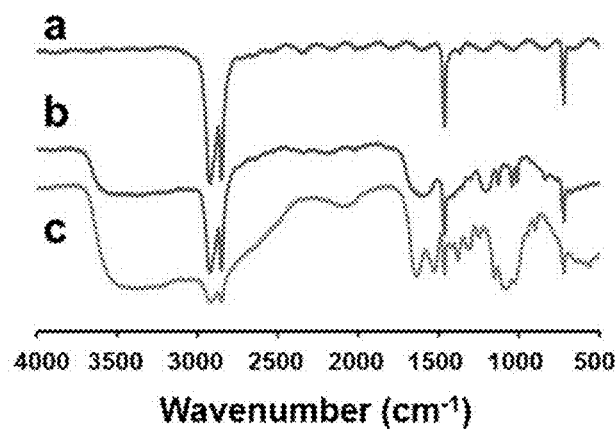
FIG. 2 shows Fouriner Transform Infrared (FTIR) spectra of (a) chemically reduced graphene oxide (CRGO), (b) CRGO-COOH, and (c) CMG.

CMG nanoparticles were synthesized as shown in FIG. 1. First, an aqueous dispersion of stable CRGO sheets was prepared by reducing graphene oxide with hydrazine hydrate in the presence of PSS (FIG. 1). See Cong et al, Small. 2010, 6:169-173. Second, the CRGO sheets were reacted with chloroacetic acid under strongly basic conditions to convert hydroxyl groups to carboxylic acid (COOH) moieties. See Sun et al., Nano Research. 2008. 1:203-212. FTIR spectroscopy (FIG. 2, b) showed a much stronger peak from the 3400 $cm^{-1}$ to 3000 $cm^{-1}$ of O—H stretch from carboxylic acid in CRGO-COOH than CRGO (FIG. 2, a). In addition, the C—O stretching from ether at 1126 $cm^{-1}$, the C—O stretching from acid at 1184 $cm^{-1}$, and the strong C=O stretching from acid at 1571 $cm^{-1}$ were observed with FTIR of CRGO-COOH (FIG. 2, b) thus demonstrating the COOH functionalization of CRGO. The CRGO-COOH was then conjugated with iron nanoparticles to form MG (He et al., Advanced Functional Materials. 2010. 20:453-459. Finally, in order to transport plasmid DNA, chitosan was covalently bonded to the MG in the presence of EDC and NHS to form CMG nanoparticles. FTIR spectroscopy of CMG nanoparticles (FIG. 2, c) showed a broad band at 3349 $cm^{-1}$ from stretching vibration of the combined peaks of the chitosan —$NH_2$ and —OH groups. The N—H bending vibration of the amine band at 1527 $cm^{-1}$ and the amide vibration band at 1621 $cm^{-1}$ confirmed chitosan attachment.

The size distribution and the peak hydrodynamic diameter of the different graphene nanoparticles in aqueous solution were measured using DLS (FIGS. 5A-5F). The average hydrodynamic diameter of CRGO, about 126 nm, is much smaller than graphene oxide, about 217 nm. When graphene oxide was reduced, there were more hydrophilic groups such as OH or $NH_2$ on the surface of the graphene sheet, which makes it more water soluble and less likely to aggregate. When CRGO is converted to CRGO-COOH, the large number of negatively charged COOH groups prevent aggregation, thus making the size of CRGO-COOH (about 93.3 nm) smaller than CRGO. When iron nanoparticles are incorporated into graphene sheets at about 278° C. the sheets aggregate into larger nanoparticles (about 207 nm) owing to the high temperature heating during the SPIO loading process. After covalent bonding of chitosan, the modified magnetic graphene particles are more soluble and their size was reduced to about 94 nm. This is significantly smaller than the 207 nm of the MG particles.

Figure 3:
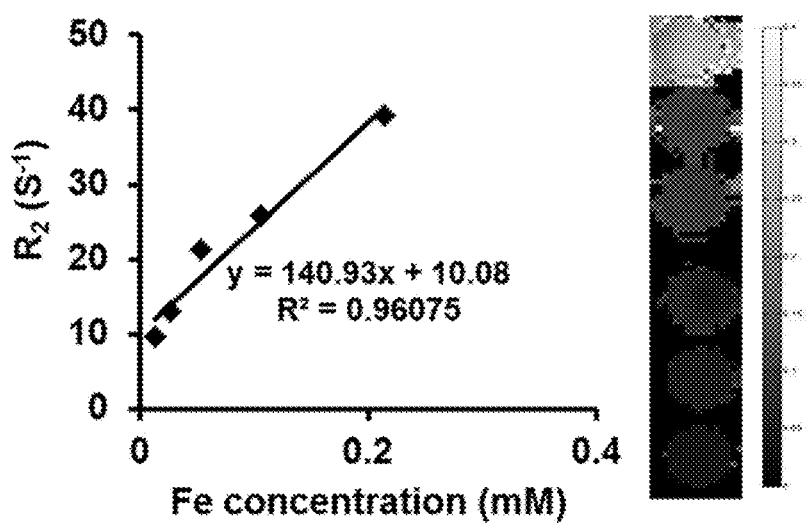
FIG. 3 shows magnetic properties of CMG with different concentrations of Fe and a T2 relaxometry map derived from multi-TE-T2 measurements.

To assess their relaxation and MRI contrast-enhancing properties, CMG nanoparticles containing different iron concentrations were subjected to MR phantom imaging. FIG. 3 shows the quantitative contrast provided by CMGs with various Fe concentrations. The $r_2$ relaxivity of CMG is 140.93 $mM^{-1} S^{-1}$ confirming that CMG has enough magnetism to perform well as an MRI contrast agent.

Example 2: Cytotoxicity and Biodistribution of CMG Nanoparticles

Materials and Methods

In vitro cytotoxicity of CMG was evaluated in human prostate cancer PC3 cells using the WST-1 colorimetric assay as described in Wang et al., J. Controlled Release. 2012. 163:82-92. Cell viability (%) was calculated according to the following equation:

$$\text{Cell Viability (\%)} = \frac{A450 \text{ sample}}{A450 \text{ control}} \times 100$$

In vitro cytotoxicity of DOX-CMG was tested on A549 cells using the Presto Blue assay (Life technologies™). About 15,000 cells/well were seeded in 10% FBS DMEM on 96-well plates at about 37° C. in a humidified atmosphere containing about 5% $CO_2$ for one day to allow adherence. Various concentrations of doxorubicin (DOX)-CMG and free DOX were added to the wells in triplicate. The cells were cultured for about 72 h at about 37° C. under about 5% $CO_2$. After about 72 h, about 10 µL of Presto Blue™ reagent (Life Technologies™) was added and cells were incubated for about 10 min. Cell viability was determined by measuring fluorescence at 535 nm in a microplate reader (Synergy H4, Biotek).

Ex Vivo MRI

The CMG nanoparticles (about 100 µl, about 3 µM Fe) were administered to six-month-old transgenic adenocarcinoma of mouse prostate tumor bearing (TRAMP) mice (n=4) by I.V. administration. After 4 h administration, the mice were euthanized and the prostate tumors were removed. Each prostate tumor was cut into two pieces. A portion of a piece of tumor was fixed in about 10% neutral buffered formalin v/v for Prussian blue staining as described below. Another portion was fixed in Fomblin® reagent (Ausimount, Thorofare, N.J., USA), which provides a completely dark background on an MRI image. MR images were obtained using a fast spin-echo (FSE) sequence using an Agilent ASR310 7-Tesla, high-field MRI scanner. The scanning parameters were slice thickness about 0.5 mm, 3 slices, field of view 80×40 mm, matrix 256×128, TR=4000 ms, TE=41.31 ms, 1 average. Signal intensity (SI) was measured within the whole imaged organ as the region of interest (ROIs). The mean value was chose for comparison of the CMG nanoparticles treated mice with the control mice. The kidney was also imaged with the same procedure.

Prussian Blue Staining for Detection of Iron

The prostate tumor and other organs kept in the formalin were saturated with increasing sucrose concentrations (about 20% to about 30%) in phosphate buffered saline (PBS). The tissues were then embedded in optimal cutting temperature compound (OCT) and frozen on dry ice. Cryosections about 20 µm thick were made, thaw-mounted onto glass slides, and stored at about −20° C. prior to staining. Slide mounted sections were placed in a Coplin jar containing a freshly prepared about 1:1 mixture of about 5% potassium ferrocyanide and about 5M HCl acid for about 72 h. The slides were then rinsed well with distilled water and counterstained with nuclear fast red (Vector Laboratories, Burlingame, Calif., USA), dehydrated with graded alcohols, cleared with xylene and mounted with Vectamount™ mounting medium.

Statistical Analysis

Statistical analysis of the data was carried out using Student's t-test. Data are expressed as means plus or minus standard deviation. Difference was considered statistically significant when the p<0.05.

Results

Figure 4:
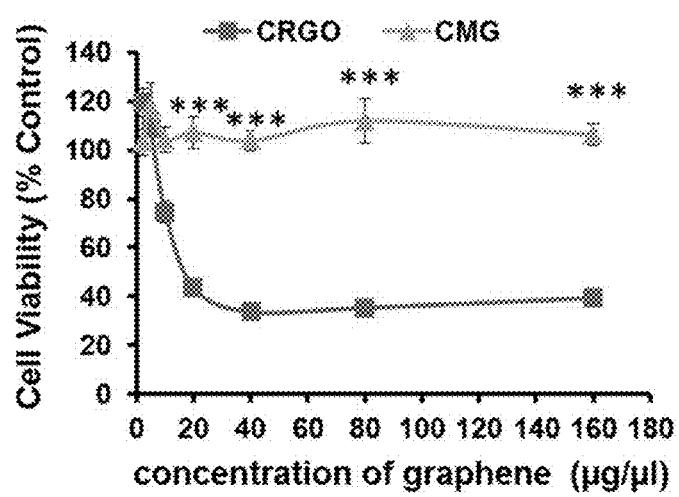
FIG. 4 shows the viability of PC3 cells treated with different concentrations of CRGO and CMG (*** $p<0.00001$).
Figure 5:
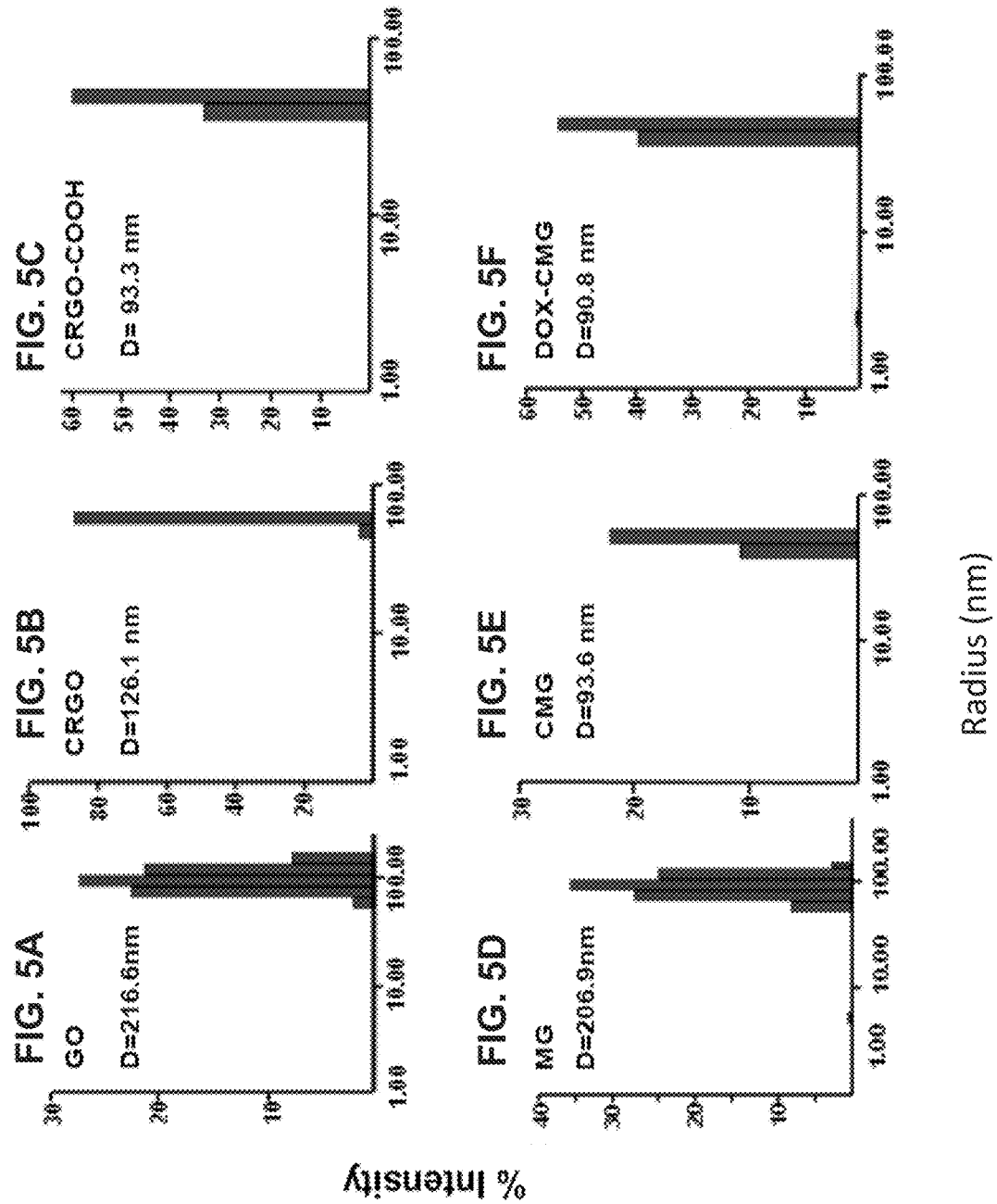
FIGS. 5A-5F show the size distribution of graphene oxide (GO) (5A), CRGO (5B), CRGO-COOH (5C), MG (5D), CMG (5E), and doxorubicin-CMG (5F).

To investigate the cytotoxicity of CMG nanoparticles, cell viability was determined by WST-1 cell proliferation assay. PC3 human prostate cancer cells were incubated in the presence of different concentrations of graphene oxide and CMG nanoparticles for 72 h. The viability of control cells not exposed to nanoparticles was set at 100%. Graphene oxide showed a dose-dependent increase in cytotoxicity (FIG. 4). However, CMG nanoparticles did not show any toxicity at the concentrations tested.

Figure 6:
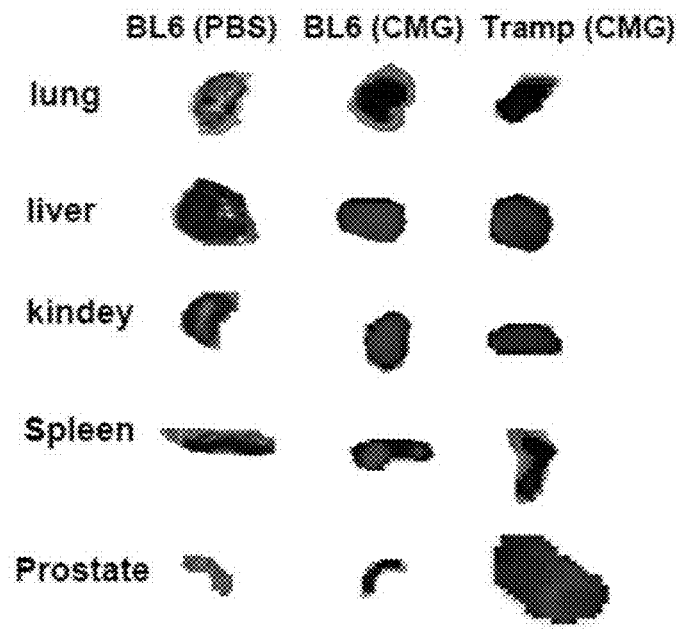
FIG. 6 shows representative results from ex vivo florescence images of organs (lung, liver, kidney, spleen, and prostate) from mice (BL6 and transgenic adenocarcinoma of mouse prostate tumor bearing (TRAMP) mice) harvested 4 h post intravenous (I.V.) injection of Cy5.5-CMG nanoparticles or Phosphate Buffered Saline (PBS) (control).
Figure 7:
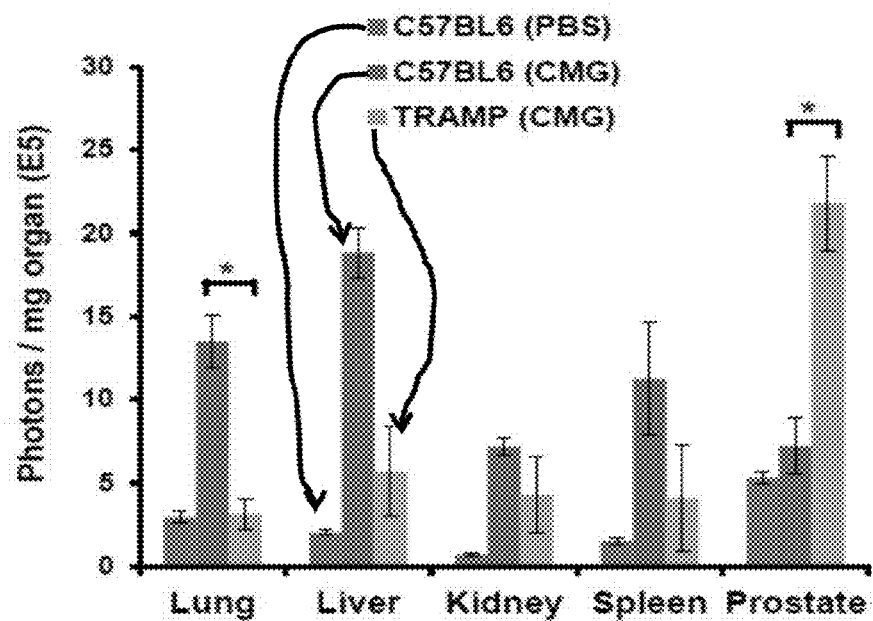
FIG. 7 shows the average fluorescence intensity of organs (lung, liver, kidney, spleen, and prostate) from mice (BL6 and TRAMP) harvested 4 h post I.V. injection of Cy5.5-CMG nanoparticles or PBS (control). Fluorescence was normalized to the weight of each organ. Error bars were based on six tumors per group (*p<0.05).

To determine the biodistribution of CMG nanoparticles in vivo, Cy5.5 was covalently bound to the CMG nanoparticles via amide bonding and excess removed by dialysis. The Cy5.5-CMG nanoparticles were injected I.V. into healthy C57BL/6 mice and about 16-20 week-old TRAMP mice, which spontaneously develop prostate tumors. Four hours after injection of Cy5.5-CMG nanoparticles, mice were euthanized and the lung, liver, kidney, spleen, and prostate were imaged by Xenogen (FIG. 6). A biodistribution analysis was performed by averaging the Cy5.5 fluorescent intensity of each organ normalized to the weight of the organ (FIG. 7). In healthy C57BL/6 mice, CMG particles were distributed predominantly in the liver, lung, and spleen. However, in TRAMP mice, CMG particles were mostly found in the prostate tumor suggesting high tumor accumulation of CMG nanoparticles. A similar biodistribution of Cy5.5-labeled CMG nanoparticles was also observed when they were administered via I.P. route to TRAMP mice and to mice xenografted with LLC1 tumor cells. See FIGS. 11A-11D. In TRAMP mice, CMG particles were found concentrated in the prostate tumor with less intensity in liver or kidney, but not in the spleen. In LLC1 tumor-bearing mice, CMG particles were found in the tumor but not in other organs.

Figure 8:
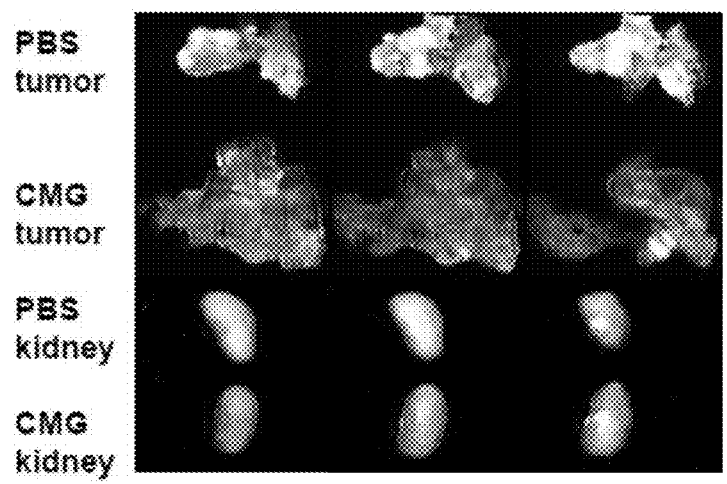
FIG. 8 shows representative ex vivo magnetic resonance (MR) images of tumor and liver tissue injected with CMG nanoparticles or PBS (control).
Figure 9:
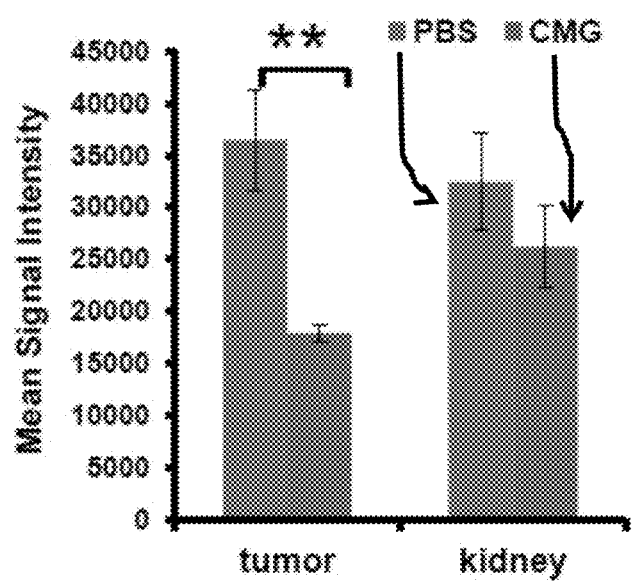
FIG. 9 shows the mean signal intensity of tumors and kidneys after I.V. administration of CMG or PBS (** p<0.01).
Figure 10:
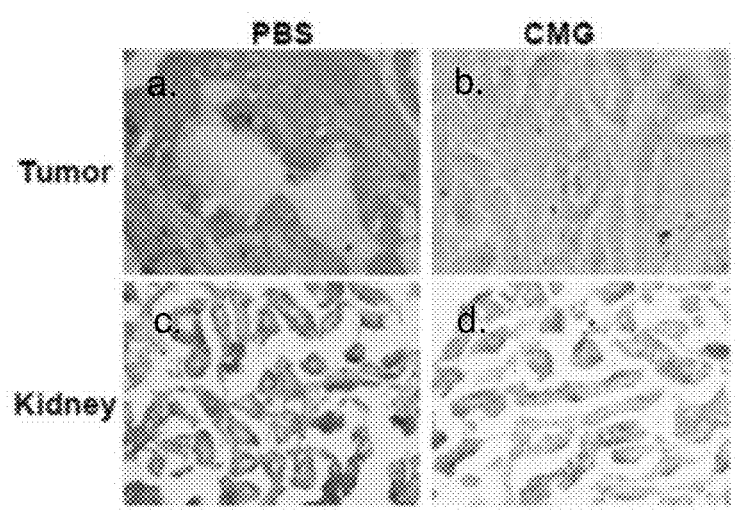
FIGS. 10A-10D show iron distribution as shown by Prussian blue staining of tumor (10A and 10B) and kidney (10C and 10D) tissue samples from a mouse that received CMG nanoparticles (10B and 10D) or PBS (10A and 10C) as a control.

Ex vivo MRI was further used to evaluate the efficiency of contrast enhancement and the targeting ability of the CMG nanoparticles for the tumor. FIGS. 8 and 9 show MRI images of tumors and livers and quantification of signal intensity respectively. MRI scans of TRAMP mice bearing prostate tumors with PBS injection showed bright signals in the tumor areas. A significant signal loss in the tumors of CMG-injected mice was observed, suggesting a T2 shortening effect of SPIO-containing CMG nanoparticles accumulated in prostate cancer (p<0.01). However, MRI images of the kidney from a prostate tumor-bearing mouse injected with CMG did not show a significant T2 effect in the tumor area compared to the control kidney. To further validate the persistence of CMG nanoparticles in the tumor, images of Prussian blue staining of tissue slices were examined. Positive blue staining in the tumors of CMG-treated mice indicates the presence of iron. There is no blue stain observed in the control tumor indicating no iron present.

Example 3: Doxorubicin Loading and In Vitro Release

Materials and Methods

DOX Loading and Release

DOX loading onto CMG nanoparticles was performed by adding different amounts of about 5 mg/ml DOX to about 1 mL CMG (about 2 mg/mL) and shaking overnight at about 4° C. Unbound DOX was removed by dialysis (SpectraPor Biotech, cellulose ester, 1000 Dalton MWCO) against deionized water at about 4° C. for about 24 h. The amount of DOX loaded onto CMG was measured by Ultra Violet (UV) absorbance at 485 nm of completely released DOX solution from nanoparticles. The drug loading as a percentage of the total particle weight was calculated by the following equation:

Drug loading (%)=(mass of DOX loaded in particles)/(mass of DOX-loaded particles)×100. The drug-release profile of DOX-CMG was determined by placing about 500 μl aliquots of DOX-CMG suspensions into a dialysis tube. The dialysis tubes were placed into about 50 mL centrifuge tubes with about 20 mL of buffer at pH about 7.4 or about 5.1 and incubated in a water bath at about 37° C. At different time points, about 1.5 mL of the solution outside of the dialysis tubes was withdrawn and the amount of DOX was determined by measuring absorption at 485 nm in a UV-Vis spectrophotometer. After measurement, the solution was placed back into the centrifuge tube. The concentration of DOX was calculated using a standard DOX concentration curve.

Statistical Analysis

Statistical analysis of the data was carried out using Student's t-test. Data are expressed as means plus or minus standard deviation. Difference was considered statistically significant when the p value was less than 0.05.

Results

Figure 12:
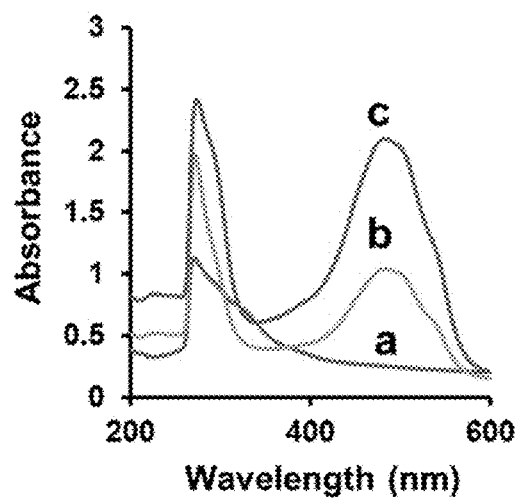
FIG. 12 shows UV-Vis absorption spectra of (a) CMG, (b) doxorubicin-CMG nanoparticles, and (c) doxorubicin alone.
Figure 13:
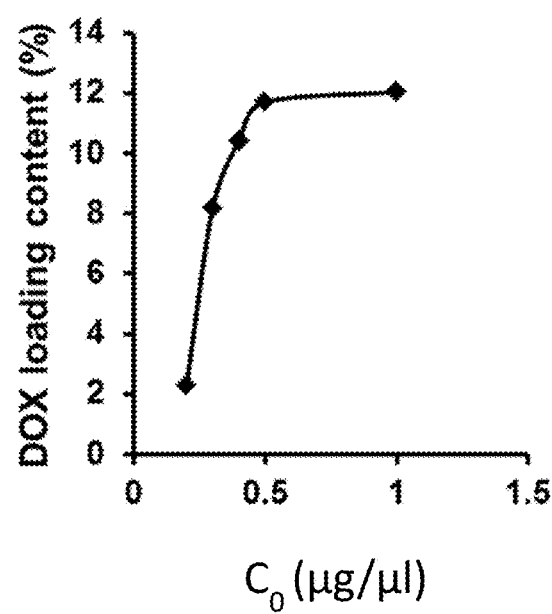
FIG. 13 shows the effect of initial doxorubicin concentration on the doxorubicin loading capacity of CMG.
Figure 14:
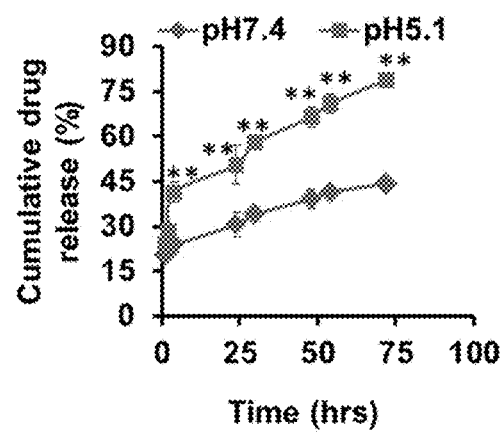
FIG. 14 shows the cumulative release of doxorubicin from doxorubicin-CMG nanoparticles at pH of about 7.4 and about 5.1 (**p<0.0001).
Figure 15:
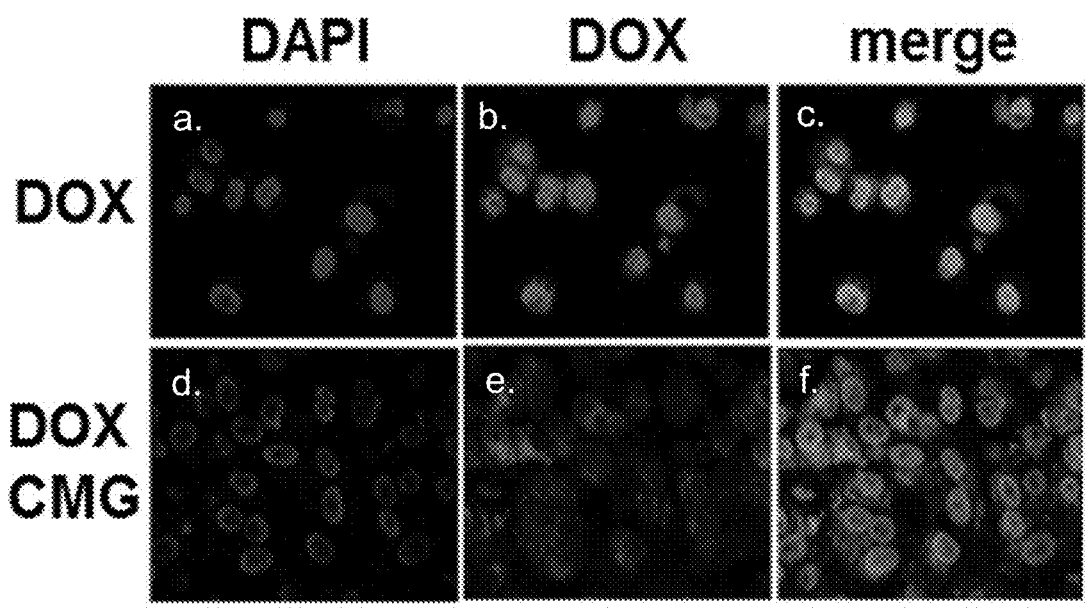
FIGS. 15A-15F show confocal microscopic images of A549cells after 20 h incubation with doxorubicin (15A-15C) or doxorubicin-CMG nanoparticles (15D-15F). Subcellular localization of doxorubicin (15B and 15E) was demonstrated via a fluorescence assay. Nuclei were stained with DAPI as a control (15A and 1D). DAPI and doxorubicin images were merged for comparison (15C-15F).
Figure 16:
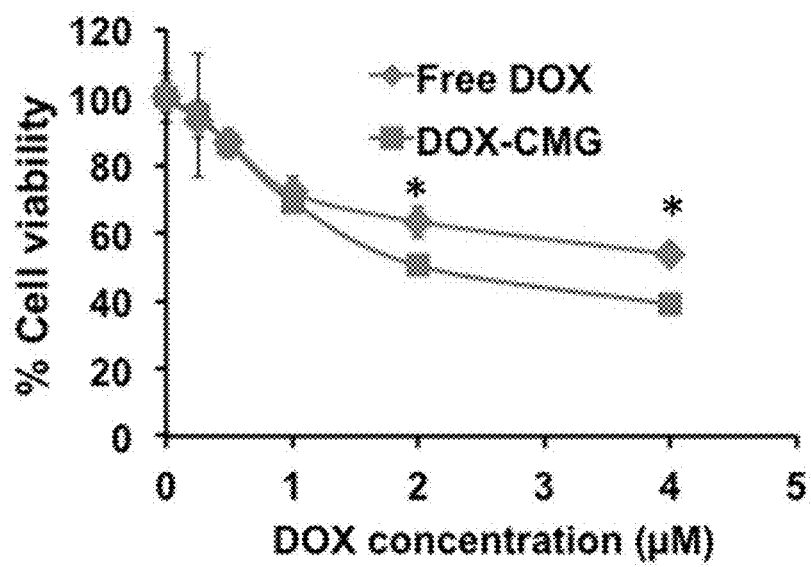
FIG. 16 shows the viability of A549 cells treated with different concentrations of doxorubicin and doxorubicin-CMG nanoparticles (*p<0.05).

To test the drug delivery capacity of CMG NPs, DOX was loaded into CMG nanoparticles by physical adsorption. The UV-Vis spectrum of DOX-CMG nanoparticles was used to confirm the loading of DOX onto CMG nanoparticles. FIG. 12 shows the UV-Vis spectrum of CMG (a), DOX-CMG (b), and DOX (c). DOX loading was confirmed by the presence of the characteristic absorbance peak of DOX-CMG at 485 nm (FIG. 12,b), which corresponded to the peak of free DOX (FIG. 12,c). The hydrodynamic diameter of DOX-loaded CMG nanoparticles was about 91 nm and was similar to the CMGs alone (FIGS. 5A-5F). The loading capacity of CMG nanoparticles for DOX was investigated by mixing a fixed concentration of CMG (2 mg/mL) with various initial DOX concentrations as shown in FIG. 13. The loading capacity of CMG for DOX increased with increasing initial DOX concentration up to about 12%. The drug-release kinetics of DOX-CMG nanoparticles was determined at pH about 5.1 and about 7.4 (FIG. 14). After 72 h, about 80% of DOX was released at pH 5.1 but only about 45% at pH 7.4, suggesting pH-dependent drug release from CMG nanoparticles. To verify the feasibility of using CMG nanoparticles for cancer therapy, the cellular uptake and intracellular drug release behaviors were investigated by confocal laser scanning microscopy in A549 lung cancer cells (FIGS. 15A-15F). After 20 h incubation, DOX was concentrated in the nuclei of cells treated with free DOX. With DOX-CMG, however, the DOX was observed mostly in the cytoplasm and only weakly in the nucleus. To determine the effectiveness of the DOX-CMG nanoparticles in killing A549 cancer cells, cells were treated with DOX-CMG nanoparticles with increasing concentrations of DOX, or free DOX, for about 72 h and analyzed using the Presto Blue cell viability assay. As shown in FIG. 16, the DOX-CMG nanoparticles were more cytotoxic to tumor cells than free DOX with the $IC_{50}$ of DOX-CMG being about 2 μM, which is about half the $IC_{50}$ of free DOX.

Example 4: Gene Delivery Potential of CMG Nanoparticles

Materials and Methods

Preparation of DNA-CMG Complex and Gel Retardation Assay

To test the ability of CMGs to form stable complexes with DNA, different weight ratios of a plasmid DNA solution (about 0.2 μg/mL) were added drop wise to a CMG solution (about 2 μg/mL) and vortexed for about 20 minutes at room temperature. The CMG-DNA complexes were mixed with loading buffer and loaded onto an 0.8% agarose gel containing ethidium bromide. Gels were electrophoresed at room temperature in Tris/borate/EDTA buffer at about 80 V for about 60 min. DNA bands were visualized using a ChemiDoc™ XRS imaging system (Bio-RAD, CA, USA). The presence of a slow-running DNA band indicates protection of the plasmid by the nanoparticles.

In Vitro Transfection of A549 or C4-2b Cells with CMG-DNA Complexes

Cells were seeded into a 96-well plate at a density of about 5000 cells per well in about 100 μl of complete medium (DMEM containing about 10% FBS, 2 mM L-glutamate, about 50 U/ml penicillin and about 50 μg/ml streptomycin). Twenty-four hours later, the medium in each well was replaced with about 500 μl of fresh complete medium and about 50 μL of CMG-DNA complexes with about 1.0 μg CMG and about 0.2 μg of plasmid DNA was added to each well. The plate was placed on a magnet for about 30 min and then incubated for about 48 h. Transfection with Lipofectamine-DNA (Lipofectamine™ LTX, Invitrogen) complexes was performed as a positive control. All transfection experiments were done in triplicate.

Statistical Analysis

Statistical analysis of the data was carried out using Student's t-test. Data are expressed as means plus or minus standard deviation. Difference was considered statistically significant when the p value was less than 0.05.

Results

Figure 17:
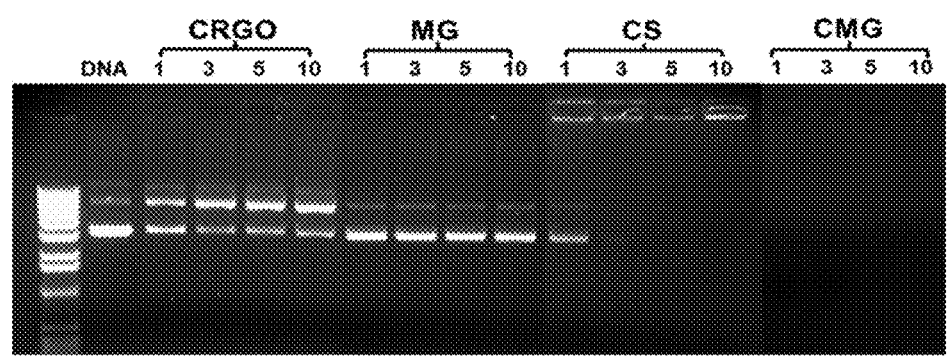
FIG. 17 shows a representative gel electrophoresis of complexes of nanoparticles and DNA at different weight rations.
Figure 18:
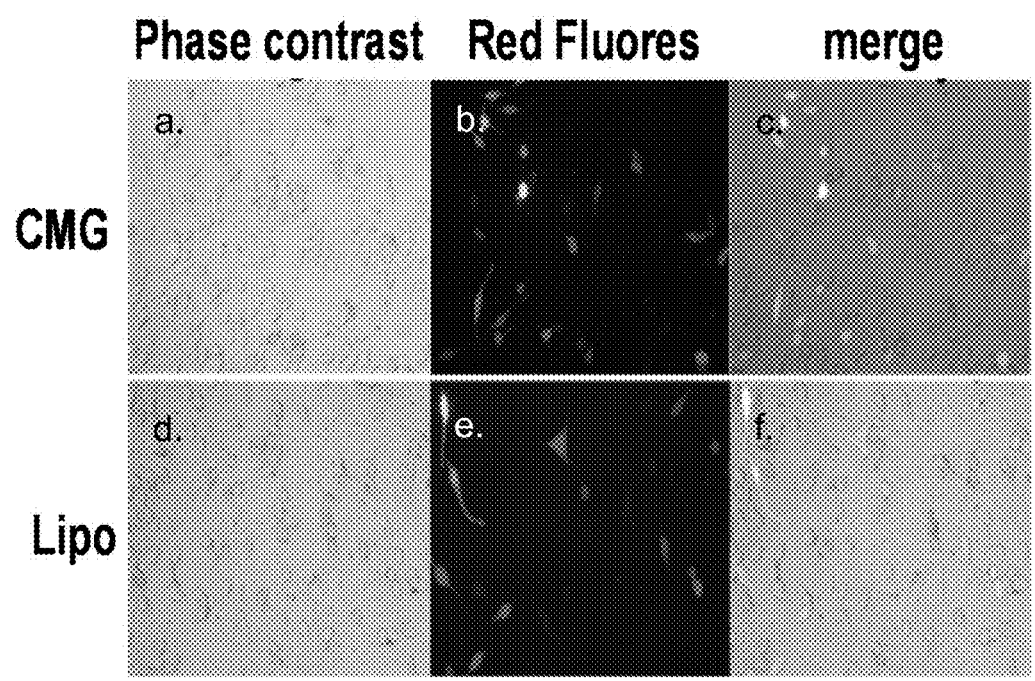
FIGS. 18A-18F show phase contrast (18A and 18D), fluorescence (18B and 18E), and merged phase contrast/fluorescence (18C-18F) microscopy images of C42b cells 48 h post-transfection with CMG nanoparticles (18A-18C) or Lipofectamine™ reagent (18D-18F) complexed with a red-fluorescent protein expression vector.

To achieve high plasmid transfection efficiency, a nanoparticle carrier needs to form a stable complex with the plasmid DNA to protect it from nucleases and lysosomal destruction. To evaluate the capability of CMG nanoparticles to form a complex with and protect plasmid DNA from digestion, the complexes were examined by agarose gel electrophoresis (FIG. 17). In this assay, DNA that binds to the nanoparticles remains in the loading wells, while unbound DNA migrates down the gel. The results show that CRGO and MG without chitosan do not bind plasmid DNA at any weight ratio. Also, the results show that chitosan alone does not completely retard DNA until the weight ratio of chitosan:DNA reaches 5:1; but CMG nanoparticles can bind DNA at a ratio as low as 1:1.

Figure 19:
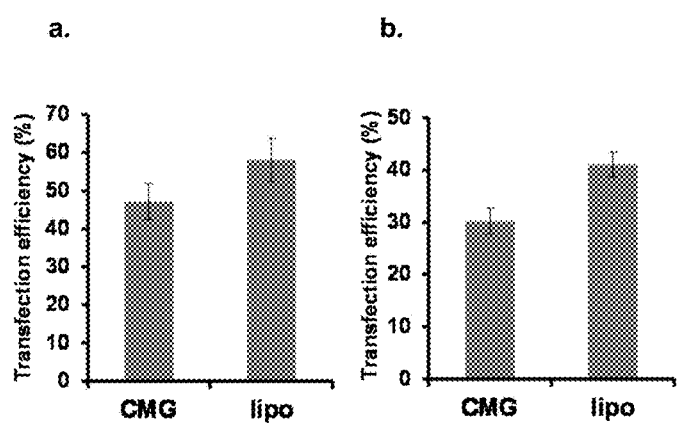
FIGS. 19A-19B show the transfection efficiency of C42b cells (19A) (p=0.37) and A549 cells (19B) (p=0.10). Transfection efficiency was quantified by Image J program.

To evaluate the gene delivery capability of CMGs, C4-2b prostate cancer cells (FIGS. 18A-18F) and A549 lung cancer cells (FIG. 19B) were incubated with CMG-DNA nanoparticles at a weight ratio of 5:1. Lipofectamine was used as a control to evaluate transfection efficiency. Forty-eight hours after transfection, the expression of red-fluorescent protein was assessed by fluorescent microscopy. As shown in FIG. 19A, about 45% of C4-2b cells were transfected with CMG nanoparticles as compared to about 55% with Lipofectamine™ reagent. Similar results were obtained with A549 cells.

Example 5: In Vivo Drug and Gene Delivery

Materials and Methods

Biodistribution of Fluorescent-Labeled CMG Nanoparticles in Mice

All mice were maintained in a pathogen-free environment and all procedures were reviewed and approved by the University of South Florida Institutional Animal Care and Use Committee. CMGs were labeled with the fluorophore Cy5.5 by reacting Cy5.5-NHS with CMGs overnight and then were purified by dialysis overnight in a dialysis membrane with molecular weight cutoff of about 1K. About 100 μl of Cy5.5-CMG solution containing about 500 μg CMG and 6.25 μg Cy5.5 was intravenously administrated to TRAMP mice. After 4 h, the mice were euthanized, the organs removed, weighed, and scanned for fluorescence using a Xenogen IVIS® imager (Caliper Life Sciences Inc., MA, USA).

In Vivo Delivery of DOX-CMG-GFP-DNA in Mice

About 500,000 LLC1 cells were subcutaneously injected into the left and right flanks of C57BL/6 mice and LLC1 tumors were allowed to grow for about 1 week. The DOX-CMG-GPF-DNAs (25 μg GFP-DNA/mouse) nanoparticles was administered to LLC tumor-bearing mice by I.V. administration (about 100 μl). After about 24 h or about 48 h administration, the mice were euthanized, the organs were removed and embedded in OCT freezing medium and kept at about −80° C. until needed. For analysis of GFP-DNA expression, frozen sections about 5 μm thick were fixed with about 4% paraformaldehyde for immunostained with anti-GFP and DAPI (4',6-diamidino-2-phenylindole) (Vector Lab). All images were made using an Olympus BX51 microscope equipped with a DP-72 high-resolution digital camera (Olympus Imaging America Inc., Center Valley, Pa.). Two mice per group and two tumors per mouse were used in this study.

Statistical Analysis

Statistical analysis of the data was carried out using Student's t-test. Data are expressed as means plus or minus standard deviation. Difference was considered statistically significant when the p<0.05.

Results

Figure 20:
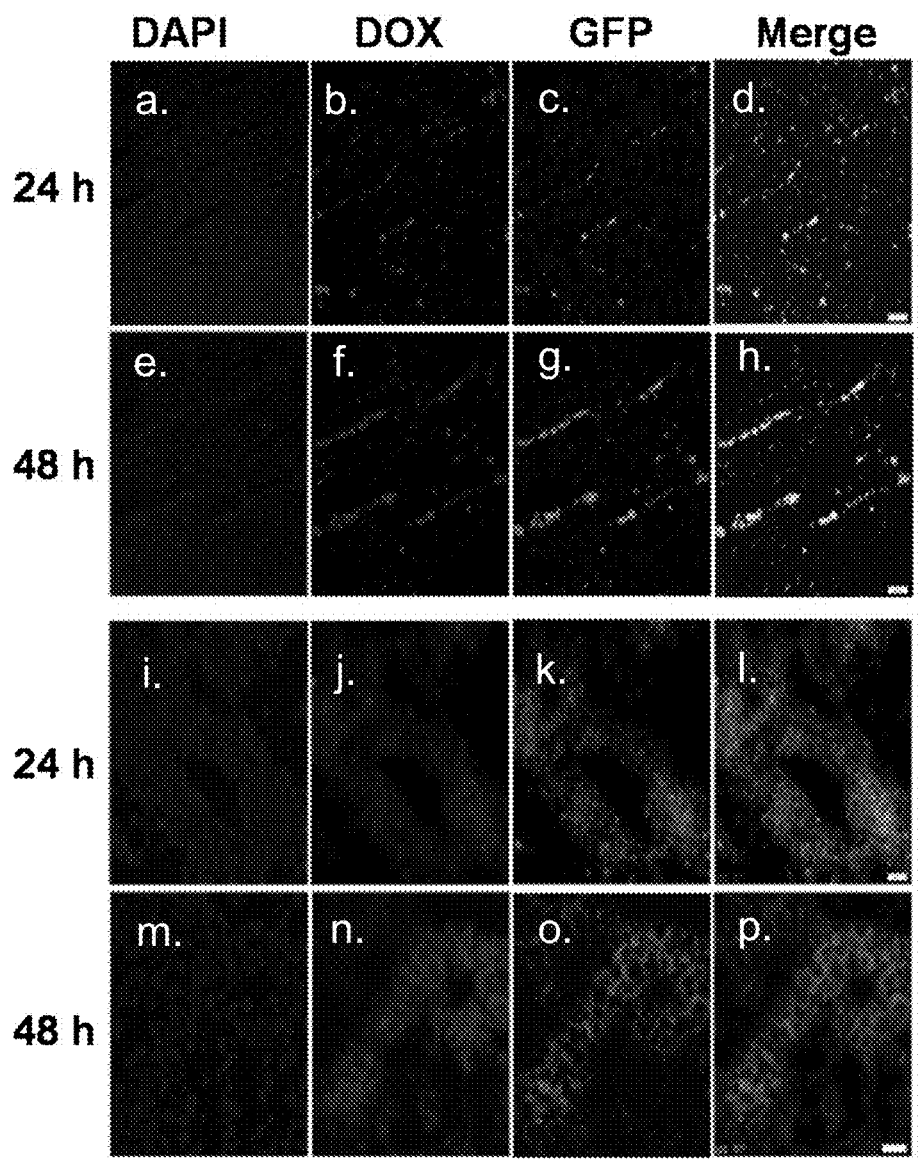
FIGS. 20A-20P show GFP expression (20C, 20G, 20K, and 20O), DAPI (20A, 20E, 20I, and 20M), doxorubicin (20B, 20F, 20J, and 20N), as indicated by a fluorescence assay, and the merged image for comparison (20D, 20H, 20L, 20P) of LLC1 tumor cells implanted on the flanks (left and right) of mice n=2. Each mouse received a single I.V. injection of doxorubicin-GMC-GFP-DNA (25 µg/mouse delivered in 100 µL). 24 h(20 20A-20D) or 48 h (20I-20L) post injection, mice were sacrificed and frozen sections were immunostained with anti-GFP antibody and nuclei were stained with DAPI. All images were taken using an Olympus BX51 microscope equipped with a DP-72 high-resolution digital camera (Olympus Imaging America Inc., Center Valley, Pa.). Images were taken under 100× magnification (20A-20H), and 400× magnification (20I-20P).
Figure 21:
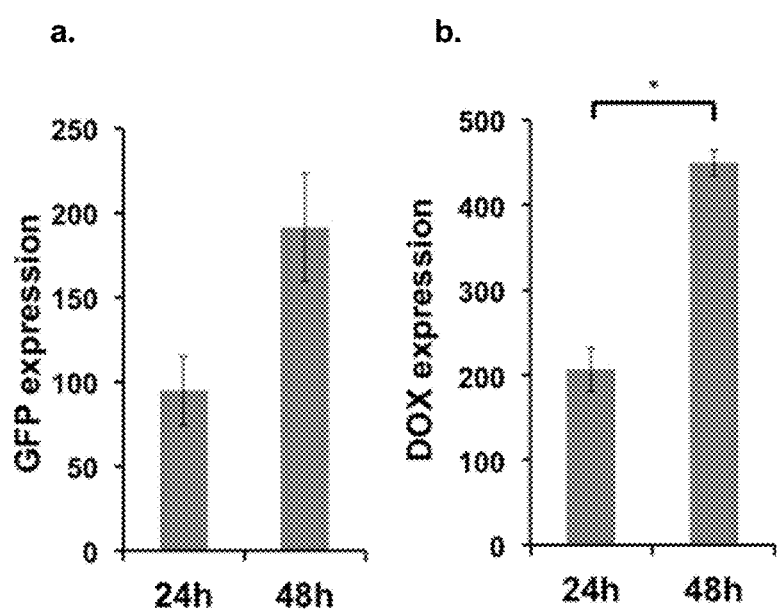
FIGS. 21A-21B show quantification of GFP expression as imaged in FIGS. 20A-20P were normalized to the control background. Normalization was completed by Image J (p=0.09). Quantification of doxorubicin fluorescence as imaged in FIGS. 20A-20P was normalized to the control background. Normalization was completed by Image J (*p<0.05).
Figure 22:
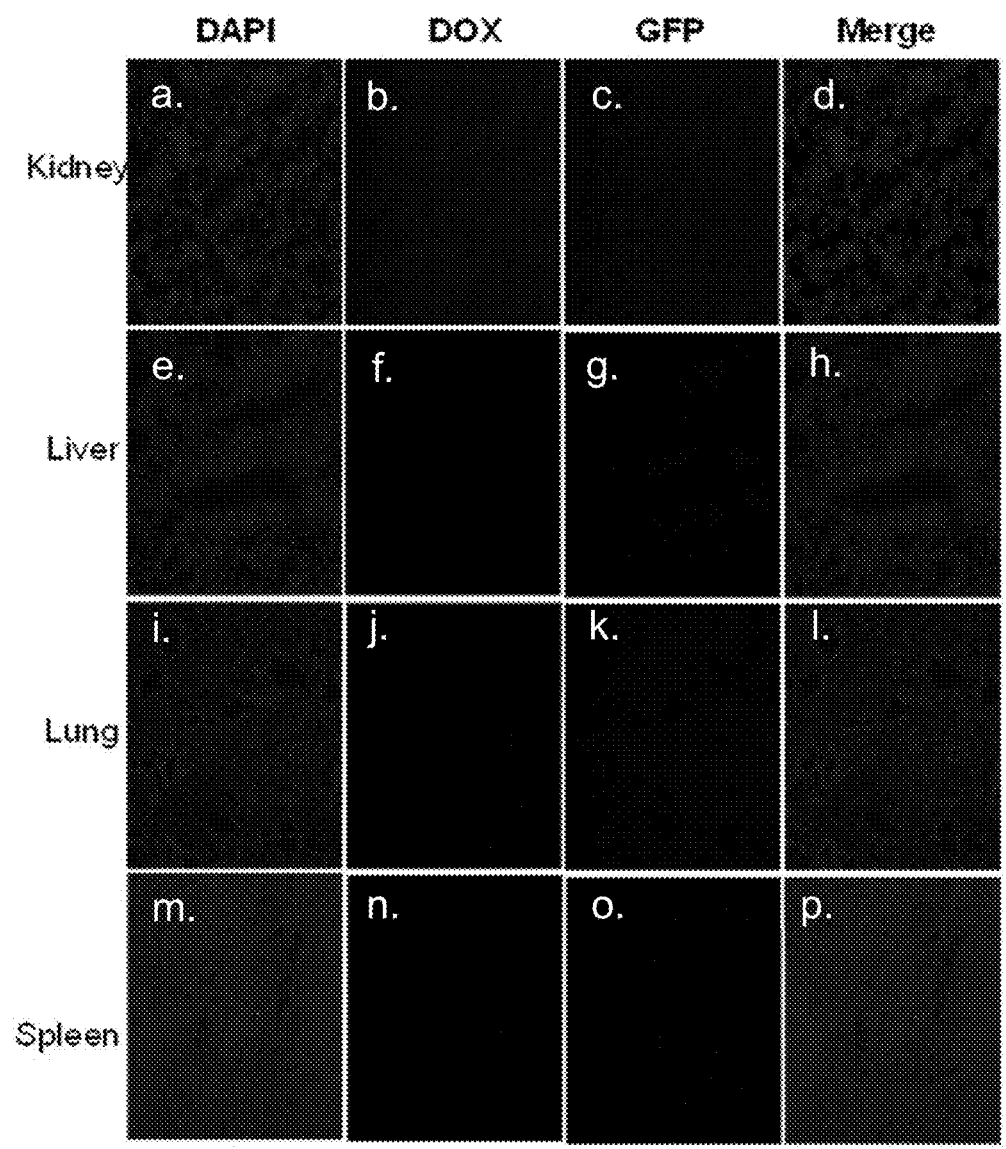
FIGS. 22A-22P show the presence of doxorubicin (22B, 22F, 22J, and 22N) and GFP expression (22C, 22G, 22K, and 22M) in organ tissue from kidney (22A-22D), liver (22E-22H), lung (22I-22L), and spleen (22M-22P) LLC1 tumor bearing mice. Mice (n=2 per group) were injected with doxorubicin-CMG-GFP DNA nanoparticles by I.V. (25 µg DNA/mouse in 100 µL). 24 or 48 h after injection, mice were sacrificed and frozen organ sections were examined for GFP expression and doxorubicin as described in relation to FIGS. 20A-20P. Images were taken at 100× magnification.
Figure 23:
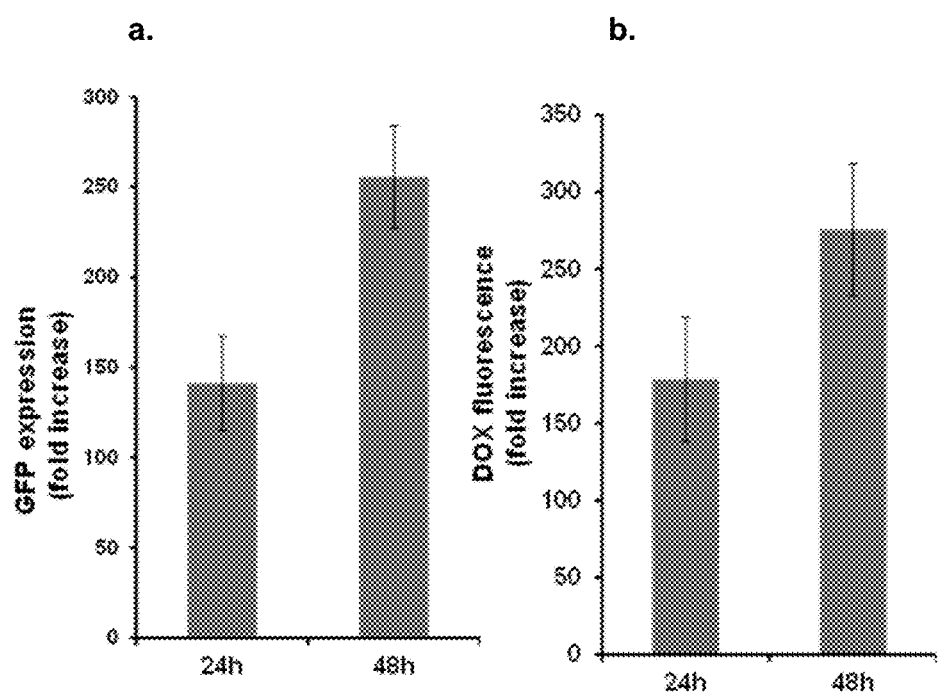
FIGS. 23A and 23B show the quantification of GFP expression (23A) and doxorubicin (F23B) from LLC1 tumor bearing mice (n=2 pre group) that received a single I.P. injection (25 µg DNA/mouse in 100 µL). 24 or 48 h after injection, mice were sacrificed and frozen organ sections were immunostained with an anti-GFP antibody and counter stained with DAPI. Quantification of GFP expression was normalized to the control background of the image J (Figure B) (p<0.05). Quantification of doxorubicin fluorescence was normalized to the control background by Image J (p<0.05).

To evaluate the potential for simultaneous drug and nucleic acid delivery by CMG nanoparticles in vivo, DOX-CMG nanoparticles were encapsulated with pDNA encoding green-fluorescent protein (GFP) and the resulting complex, DOX-CMG-GFP-DNA, was administered I.V. to LLC1 tumor bearing mice (n=4). After about 1 or 2 days, the mice treated with nanoparticles or phosphate buffered saline (PBS) (control) were euthanized and the organs and tumors were excised. Frozen sections were immunostained with anti-GFP antibody, and counterstained with DAPI, and immunostained for DOX. The expression of GFP and presence of DOX were examined by fluorescent microscopy. As shown in FIGS. 20A-20P, DOX and GFP expression was distributed throughout the tumor. Some cells show the presence of DOX and GFP expression, as judged by the colocalization of red and green fluorescence (yellow). Further, more cells show the fluorescence of DOX and/or GFP at 48 hrs after I.V. administration than at 24 hrs. In contrast to tumor tissue, other organs (liver, lung, kidney and spleen) did not show any DOX or GFP expression (FIGS. 22A-22P). Similar results were also observed for the I.P. injection of DOX-CMG-GFP nanoparticles (FIGS. 23A-23B). These results suggest that CMG nanoparticles are capable of delivering drugs and genes as payloads predominantly to tumors.

We claim:

1. A nanoparticle comprising:
   a chemically reduced graphene sheet;
   chitosan, wherein the chitosan is attached to or loaded onto the chemically reduced graphene sheet;
   a magnetic resonance imaging (MRI) contrast agent attached to or loaded onto the chemically reduced graphene sheet;
   a chemotheraputic agent attached to or loaded onto the chemically reduced graphene sheet; and
   a DNA plasmid attached to or loaded onto the chemically reduced graphene sheet.

2. The nanoparticle of claim 1, wherein the nanoparticle is a theranostic agent.

3. The nanoparticle of claim 1, wherein the MRI contrast agent is a super paramagnetic iron oxide.

4. The nanoparticle of claim 1, wherein the MRI contrast agent is a radio contrast agent.

5. The nanoparticle of claim 1, further comprising a targeting moiety attached to the chemically reduced graphene sheet.

6. A theranostic formulation comprising:
   a nanoparticle comprising:
   a chemically reduced graphene sheet;
   chitosan, wherein the chitosan is attached to or loaded onto the chemically reduced graphene sheet;
   a magnetic resonance imaging (MRI) contrast agent attached to or loaded onto the chemically reduced graphene sheet;
   a chemotherapeutic agent attached to or loaded onto the chemically reduced graphene sheet;
   a DNA plasmid attached to or loaded onto the chemically reduced graphene sheet; and
   a pharmaceutically acceptable carrier.

7. A method for generating theranostic nanoparticles comprising:
   reducing a graphene oxide sheet to form chemically reduced graphene oxide sheet;
   loading or attaching a magnetic resonance imaging (MRI) contrast agent onto the chemically reduced graphene oxide sheet;
   loading or attaching chitosan onto the chemically reduced graphene oxide sheet;
   loading or attaching a chemotherapeutic agent onto the chemically reduced graphene oxide sheet; and
   loading or attaching a DNA plasmid moiety onto the chemically reduced graphene oxide sheet.

8. The method of claim 7, further comprising the step of attaching or loading a targeting moiety onto the chemically reduced graphene oxide sheet.

* * * * *